United States Patent
D'Hoore et al.

(10) Patent No.: US 11,503,848 B2
(45) Date of Patent: Nov. 22, 2022

(54) SWEETENING AND TASTE-MASKING COMPOSITIONS, PRODUCTS AND USES THEREOF

(71) Applicant: HEALTHTECH BIO ACTIVES, S.L.U., Barcelona (ES)

(72) Inventors: Tom Nelly A. D'Hoore, Sant Cugat del Vallès (ES); Francisco Borrego Ríos, Sant Cugat del Vallès (ES); Francisco Javier Crespo Montero, Sant Cugat del Vallès (ES)

(73) Assignee: HEALTHTECH BIO ACTIVES, S.L.U, Barcelona (ES)

( * ) Notice: Subject to any disclaimer, the term of this patent is extended or adjusted under 35 U.S.C. 154(b) by 293 days.

(21) Appl. No.: 16/633,745

(22) PCT Filed: Jul. 26, 2018

(86) PCT No.: PCT/EP2018/070299
§ 371 (c)(1),
(2) Date: Jan. 24, 2020

(87) PCT Pub. No.: WO2019/020750
PCT Pub. Date: Jan. 31, 2019

(65) Prior Publication Data
US 2020/0170288 A1 Jun. 4, 2020

(30) Foreign Application Priority Data
Jul. 27, 2017 (EP) ..................... 17382503

(51) Int. Cl.
*A23L 27/30* (2016.01)
*A23L 27/00* (2016.01)
(Continued)

(52) U.S. Cl.
CPC ............... *A23L 27/33* (2016.08); *A23L 27/84* (2016.08); *A23L 27/86* (2016.08); *A23L 33/28* (2016.08); *A61K 47/40* (2013.01); *A23L 33/30* (2016.08)

(58) Field of Classification Search
CPC .......... A23L 27/33; A23L 27/84; A23L 27/86; A23L 2/60; A61K 47/40; C08L 5/16
See application file for complete search history.

(56) References Cited

U.S. PATENT DOCUMENTS

| | | | |
|---|---|---|---|
| 4,158,068 A | 6/1979 | Von Rymon Lipinski et al. | |
| 2006/0068059 A1* | 3/2006 | Boghani ................ | A23G 4/10 426/5 |

(Continued)

FOREIGN PATENT DOCUMENTS

EP 0507598 A1 10/1992

OTHER PUBLICATIONS

Chung et al., "Effect of β-Cyclodextrin on the Taste Quality of Neohesperidin Dihydrochalcone," J. Food Sci. Nutr., vol. 1, No. 2, 1996 (Jan. 1996), pp. 186-189, XP009500727.
(Continued)

*Primary Examiner* — Nikki H. Dees
(74) *Attorney, Agent, or Firm* — Birch, Stewart, Kolasch & Birch, LLP

(57) ABSTRACT

The present invention relates to a sweetening composition comprising neohesperidin dihydrochalcone (NHDC) and gamma-cyclodextrin, to the use of the sweetening composition for sweetening ingestible products, namely, food products and pharmaceuticals, and to an ingestible product comprising the sweetening composition. Furthermore, the present invention also relates to the use of a composition comprising neohesperidin dihydrochalcone and a cyclodextrin selected from beta-cyclodextrin and gamma-cyclodextrin as taste-masking agent, to a process for masking unpleasant tastes in ingestible products, namely in food products and pharmaceuticals, and to ingestible products which comprise unpleasantly tasting substances and the taste-masking composition.

11 Claims, 6 Drawing Sheets

(51) Int. Cl.
　　　*A23L 33/28*　　　(2016.01)
　　　*A61K 47/40*　　　(2006.01)
　　　*A23L 33/00*　　　(2016.01)

(56) References Cited

U.S. PATENT DOCUMENTS

2007/0275147 A1* 11/2007 Prakash ................ A23L 27/34
　　　　　　　　　　　　　　　　　　　　　　　　　　426/548
2011/0104329 A1* 5/2011 Boghani ................ A23G 9/32
　　　　　　　　　　　　　　　　　　　　　　　　　　426/3

OTHER PUBLICATIONS

Fujiwara et al., "Sweeteners Interacting with the Transmembrane Domain of the Human Sweet-taste Receptor Induce Sweet-taste Synergisms in Binary Mixtures," Food Chemistry, vol. 130, No. 3, 2012 (Available online Jul. 31, 2012), pp. 561-568, XP028288588.
International Search Report and Written Opinion of the International Searching Authority (forms PCT/ISA210, PCT/IS237 and PCT/ISA/220), dated Oct. 16, 2018, for corresponding International Application No. PCT/EP2018/070299.
Ley, "Masking Bitter Taste by Molecules," Chem. Percept., vol. 1, 2008 (Published online Feb. 13, 2008), pp. 58-77.
Munro et al., "Safety Assessment of γ-cyclodextrin," Regulatory Toxicology and Pharmacology, vol. 39, No. Supplement 1, 2004 (Available online Jun. 10, 2004), pp. S3-S13, XP008141425.

* cited by examiner

SWEETENING AND TASTE-MASKING COMPOSITIONS, PRODUCTS AND USES THEREOF

This application claims the benefit of European Patent Application EP 17382503.5 filed on Jul. 27, 2017.

TECHNICAL FIELD

The present invention relates to the field of sweetening and taste-masking, in particular, it relates to sweetening and taste-making compositions comprising neohesperidin dihydrochalcone.

BACKGROUND ART

The consumption of sugar-sweetened food products and beverages has been linked to increased risk of obesity, diabetes and heart disease, and is also detrimental to dental health. Therefore, it is nowadays generally accepted that the consumption of sucrose, as well as of other caloric sweeteners, such as glucose, fructose or high-fructose corn syrups, must be reduced.

This need to reduce sugar consumption has boosted the use of low-calorie sweeteners, such as stevia extract, monk fruit, saccharin, aspartame, acesulfame K, cyclamate, sucralose or neohesperidin dihydrochalcone, among others.

In particular, neohesperidin dihydrochalcone (also known as neohesperidin DC or NHDC) is a well-known low-calorie sweetener which is a derivative of the natural product neohesperidin, a flavanone found in citrus fruits. It is a high intensity sweetener, being about 1500 times sweeter than sucrose, and it is useful for sweetening food, beverages, as well as pharmaceutical products.

However, the use of high-intensity low-calorie sweeteners as sugar substitutes entails several challenges, because not only is sweetness intensity important but other organoleptic properties are also required. Thus, it is generally accepted that an ideal sweetener should have a pleasant taste, with immediate onset and without lingering aftertaste. In fact, the more a sweetener tastes and functions like sucrose, the greater the consumer acceptability. On the other hand, it is also desirable, for economic reasons, to achieve the desired sweetness level using the minimum amount of sweetener.

Hence, for instance, although neohesperidin dihydrochalcone is intensely sweet, it has the drawback of having a relatively delayed onset of sweetness and a liquorice-like lingering aftertaste, which hampers a wider usage as sugar substitute.

Several solutions have been proposed so far in the state of the art in order to overcome those drawbacks and to improve the taste profile of low-calorie sweeteners, in particular, of neohesperidin dihydrochalcone.

A first strategy combines low-calorie sweeteners with caloric sweeteners. The low-calorie sweeteners allow to reduce caloric sweeteners to a certain extent. On the other hand, the amount of low-calorie sweetener is sufficiently low, so that it does not significantly impact the sweetening profile of the resulting sweetener blend. In this context, neohesperidin dihydrochalcone is a very interesting candidate low-calorie sweetener as it has very strong synergies with caloric sweeteners. These synergies allow higher than expected caloric sweetener reductions without jeopardizing the sweetening profile. There is of course an interest and need to further increase these synergies in order to further reduce the caloric sweeteners.

A second strategy is to use blends of two or more low-calorie sweeteners, since a number of those blends results in a synergic effect, so the desired level of sweetness can be achieved using lower amounts of sweeteners, thus resulting in cost savings. Moreover, some of those blends also provide a qualitative synergy, i.e., the taste quality of the blends is often better than that of the individual components, for example, the undesirable aftertastes may be reduced.

For example, U.S. Pat. No. 4,158,068 discloses that the use of a mixture of acesulfame K with other sweeteners, for example, with neohesperidin DC, provides a sweet taste that is more saccharose-like than when using the sweeteners individually.

Moreover, European patent application EP0507598-A1 discloses that the combination of neohesperidin DC and sucralose provides synergy and also an improvement in the sweetness quality.

In the article Chung H. J., *The effect of β-cyclodextrin on the taste quality of neohesperidin dihydrochalcone*, J. Food Sci. Nutr., 1996, 1(2), 186-189, the effect of beta-cyclodextrin on the sweetness and aftertaste of NHDC was investigated, and it was concluded that the addition of beta-cyclodextrin reduced both the intensity of sweetness and the aftertaste of NHDC. It was found that the intensity of sweetness decreased more rapidly than the aftertaste. The author thus concluded that it was not possible to suppress the aftertaste of NHDC while maintaining the sweet taste by using beta-cyclodextrin. In other words, the sweet quality of the resulting mixture was inferior to that of NHDC alone.

Therefore, there is a need in the art for new high-intensity sweetening compositions with improved characteristics, namely, which are able to provide the desired sweet taste with the minimum amount of sweetener, and having an improved taste-quality, free of after-tastes and more similar to the taste of sucrose.

On the other hand, another related problem arises due to the unpleasant taste of a number of substances which are frequently found in food, beverages and pharmaceutical products.

The main tastes or taste sensations that are typically perceived as unpleasant are bitterness, astringency and metallic tastes.

Only rarely consumers accept the bitter/astringent taste of food and beverages, for example, in black coffee, black or green tea, beer, red wine, grapefruit products or bitter lemon. In most other cases, those tastes are not desirable and must be eliminated or masked.

For example, many substances regarded as healthy and purposely added to healthy food preparations are however perceived adversely in terms of taste by the consumers. This may be the case of the bitter taste of certain vitamins, minerals, peptides or protein hydrolysates or the bitter or astringent taste of certain plant-based phenols, flavonoids, isoflavones, terpenes and glucosinolates, which are reported to have positive antioxidant and anticarcinogenic properties.

Another example is the bitter aftertaste associated to potassium chloride, which is increasingly being used to provide saltiness to food products, as a healthier sodium chloride replacer.

A particularly problematic group of consumables in terms of taste are pharmaceutical products, which frequently contain active ingredients having bitter, astringent or metallic tastes. This adverse perception may even adversely affect the patient compliance, especially in those population groups which are particularly sensitive to bad tastes, particularly, to children.

Consequently, since the taste of the consumable product plays an important role in their acceptance by the consumer, efforts have been made to suppress or reduce those unpleasant tastes in consumables, namely, in food, beverages and pharmaceutical products.

Depending on each particular substance and on each particular consumable product, different taste-masking solutions may be used, as have been extensively reported in the prior art, for example, some possible strategies are partly removing the bittering substances, coating or microencapsulating them, adding flavours and/or sweeteners, or adding specific taste-masking substances.

The use of taste-masking substances, which are able to modulate, reduce or suppress unpleasant tastes, particularly, bitterness, astringency or metallic tastes, has proved to be useful for many particular applications.

A good number of substances have been reported in the art for use as taste-masking agents in food and pharmaceuticals as reviewed, for example, by Ley J. P. in the article *Masking bitter taste by molecules*, Chem. Percept., 2008, 1, 58-77. Among the many taste-masking substances cited are some sweeteners, such as thaumatin and neohesperidin dihydrochalcone; polymers and complexing agents, such as cyclodextrins, poly-γ-glutamic acid and chitosan; neodiosmin; L-ornithine and derivatives such as L-ornithyl-β-alanine or L-ornithinyltaurine; several dipeptides containing aspartic acid such L-aspartyl-L-phenylalanine potassium salt; sodium salts of saturated fatty acids, such as sodium stearate, palmitate and laurate; organic phosphates, phosphonates, vanadates, thiophosphates, and biphosphates; flavanones such as eriodictyol and homoeriodictyol; among many others.

In particular, neohesperidin dihydrochalcone has been reported as an effective taste-masking substance, for example, it has been used for masking the bitter taste of substances like paracetamol, dextromethorphan and other pharmaceuticals, as well as in special foods, as disclosed in Borrego et al., *Neohesperidin Dihydrochalcone*, in: L O'Brien Nabors, eds. Alternative Sweeteners, Fourth Edition, CRC Press, 2012, 94-95.

However, achieving an acceptable level of taste-masking usually requires the use of considerable amounts of the taste-masking substance, which is unsatisfactory in terms of costs and additional off-notes.

Therefore, there is a need in the art for new taste-masking compositions, which are able to effectively modulate, reduce or suppress unpleasant tastes and require the use of reduced amounts of the taste-masking composition.

OBJECT OF THE INVENTION

Figure 1:
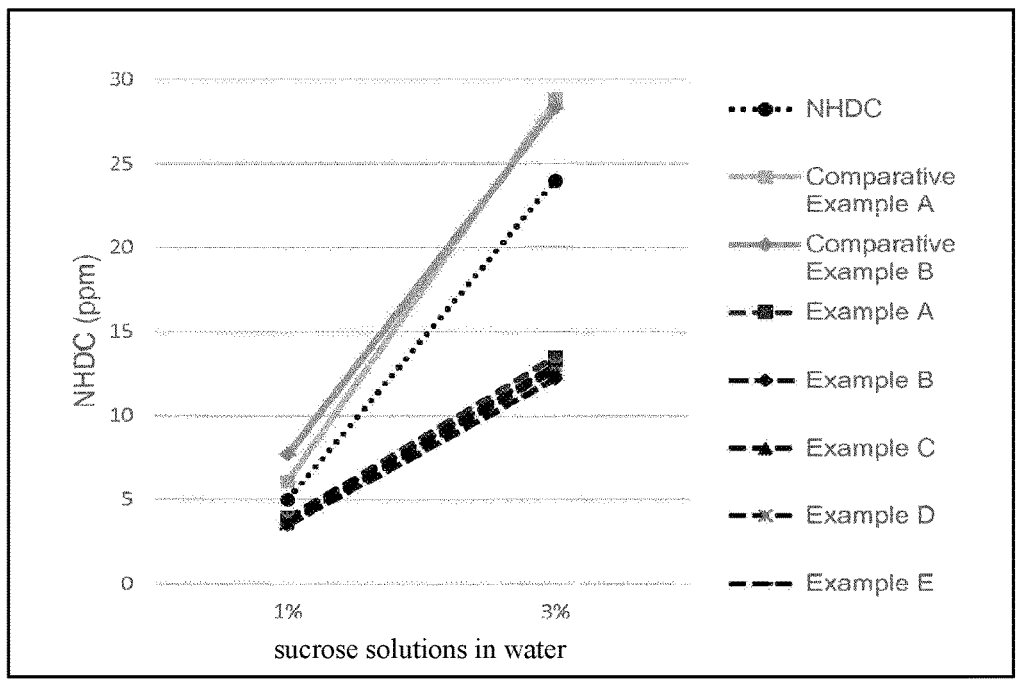
FIG. 1 represents the concentrations of neohesperidin dihydrochalcone (NHDC) which are equisweet to 1% and 3% sucrose solutions in water. The abscissa represents the two sweetness levels evaluated, i.e., 1% and 3% sucrose solutions, and the ordinate represents the NHDC concentrations needed to reach these sweetness levels. In successive tests, neohesperidin dihydrochalcone was used alone (NHDC, black circles), in combination with gamma-cyclodextrin (black squares, diamonds, triangles, crosses and straight line—Ex. A-E), and in combination with beta-cyclodextrin (grey squares and diamonds). A partial overlapping is observed between lines corresponding to Examples D (NHDC:gCD 1:6) and E (NHDC:gCD 1:10).

In a first aspect, the present invention relates to a sweetening composition comprising neohesperidin dihydrochalcone and gamma-cyclodextrin.

A second aspect of the invention relates to the use of a composition comprising neohesperidin dihydrochalcone and a cyclodextrin selected from beta-cyclodextrin and gamma-cyclodextrin as taste-masking agent.

A further aspect of the invention relates to the use of the sweetening composition for sweetening ingestible products.

A further aspect of the invention relates to an ingestible product comprising the sweetening composition.

A further aspect of the invention relates to an ingestible product which comprises an unpleasantly tasting substance and a taste-masking composition comprising neohesperidin dihydrochalcone and a cyclodextrin selected from beta- and gamma-cyclodextrin.

DETAILED DESCRIPTION OF THE INVENTION

In a first aspect, the present invention relates to a sweetening composition comprising neohesperidin dihydrochalcone and gamma-cyclodextrin.

In a second aspect, the invention relates to the use of a composition comprising neohesperidin dihydrochalcone and a cyclodextrin selected from beta-cyclodextrin and gamma-cyclodextrin as taste-masking agent.

The authors of the present invention have developed a new sweetening composition comprising the combination of neohesperidin dihydrochalcone (NHDC) and gamma-cyclodextrin which, surprisingly, provides an outstanding synergistic effect, thus achieving the desired sweetness level using less amount of NHDC. Moreover, not only the sweetness intensity is synergically increased, but also the sweetness quality of the combination is remarkably superior to using NHDC alone, for example, the lingering aftertaste is greatly reduced, and the onset time is also decreased, thus providing a better overall taste profile, more similar to that provided with sucrose.

Furthermore, it was also surprisingly discovered that compositions comprising the combination of NHDC with either beta-cyclodextrin or gamma-cyclodextrin show strong taste-masking synergy, that is to say, the taste-masking effect achieved with the combination, typically for masking bitter or astringent tastes, is higher than the sum of the effects of each individual substance.

Along the present description, as well as in the claims, the singular forms, usually preceded by "a", "an" or "the", are to be construed to include also the plural, unless the context clearly indicates otherwise.

As used herein, the term "about" used before a quantitative value is to be construed as including the specific quantitative value and also a variation of no more than ±10% of the given value, preferably of no more than ±5% of the given value.

Neohesperidin Dihydrochalcone

Neohesperidin dihydrochalcone (CAS number 20702-77-6) is a well-known synthetic intense sweetening agent, sometimes abbreviated as neohesperidin DC or NHDC. It is also known by its chemical name 1-[4-[[2-O-(6-Deoxy-α-L-mannopyranosyl)-β-D-glucopyranosyl]oxy]-2,6-dihydroxyphenyl]-3-(3-hydroxy-4-methoxyphenyl)propan-1-one.

Structurally, it is an analogue of neohesperidin, a bitter flavanone that occurs in citrus fruits. NHDC can be synthesized, either from naringin, which is obtained from grape fruit (*Citrus paradisi*), or from neohesperidin, which can be extracted from bitter orange (*Citrus aurantium*), as reviewed, for example, in Borrego et al., *Neohesperidin Dihydrochalcone*, in: L O'Brien Nabors, eds. Alternative Sweeteners, Fourth Edition, CRC Press, 2012, 117-131.

Moreover, NHDC is widely available commercially, for example, from the company Interquim S.A, or Ferrer HealthTech.

Cyclodextrin

Cyclodextrins are cyclic oligosaccharides derived from starch. The cyclic structure of cyclodextrins is generally described as having a conic or torus-like shape, wherein the primary and secondary hydroxyl groups are orientated to the exterior, while nonpolar hydrogens and ether-like oxygens are at the inside of the molecule, thus forming a hydrophilic external surface and a nonpolar, hydrophobic internal cavity.

As a result of this three-dimensional structure, cyclodextrins are able to act as hosts to form inclusion complexes with a wide variety of guest molecules, generally hydrophobic molecules or molecules comprising a hydrophobic part. In these inclusion complexes, the guest molecule is held, at least in part, within the hydrophobic cavity of the cyclodextrin host molecule.

In particular gamma-cyclodextrin (γ-cyclodextrin, CAS number 17465-86-0), also known as cyclomaltooctaose or cyclooctaamylose, is a cyclodextrin containing of 8 (1→4)-linked α-D-glucopyranosyl units.

Gamma-Cyclodextrin can be obtained from starch by the action of the enzyme cyclodextrin glycosyltransferase (CDTGase; ED 2.4.1.19), for example as disclosed in Hedges A, *Cyclodextrins: Properties and Applications*, In: Starch. Chemistry and Technology, BeMiller J and Whistler R, eds., Food Science and Technology International Series, Third Edition, Elsevier, 2009, 833-851.

Gamma-Cyclodextrin is readily available from several commercial sources, for example, from the companies Wacker Chemie and Roquette.

Beta-Cyclodextrin (β-cyclodextrin, CAS number 7585-39-9), also known as beta-cycloamylose, beta-dextrin, beta-dexum, cycloheptaamylose, cycloheptaglucan or cyclomaltoheptose, is a cyclodextrin containing of 7 (1→4)-linked α-D-glucopyranosyl units.

Beta-Cyclodextrin can be obtained from starch by the action of the enzyme cyclodextrin glycosyltransferase (CDTGase; ED 2.4.1.19), for example as disclosed in Hedges A, Cyclodextrins: Properties and Applications, In: Starch. Chemistry and Technology, BeMiller J and Whistler R, eds., Food Science and Technology International Series, Third Edition, Elsevier, 2009, 833-851.

Beta-Cyclodextrin is readily available from several commercial sources, for example, from the companies Wacker Chemie and Roquette.

Sweetening Composition

The sweetening composition of the present invention comprises neohesperidin dihydrochalcone and gamma-cyclodextrin.

This sweetening composition is meant to include a plain mixture of neohesperidin dihydrochalcone and gamma-cyclodextrin, as well as when both components are in the form of a complex.

In one embodiment, the sweetening composition is a mixture of both components.

The composition according to this embodiment can be prepared by simple dry blending of NHDC and gamma-cyclodextrin using any suitable blending means, for example, using a tumbling mixer or agitator mixer.

In another embodiment of the invention, NHDC and gamma-cyclodextrin are in the form of a complex.

In this complex, NHDC is presumably inserted, at least partially, into the cavity of gamma-cyclodextrin, forming an inclusion complex. However, the term "complex", within the meaning of the present invention, is meant to include other possible variations, involving further non-stoichiometric interactions between NHDC and gamma-CD to form the supramolecular complex.

This complex is typically prepared by dissolving gamma-cyclodextrin in a suitable solvent, preferably in water, and subsequently adding NHDC to the solution and isolating the complex from the solution.

The concentration of gamma-cyclodextrin in the solution is generally comprised between 1-20% w/v, preferably between 5-10% w/v. The NHDC is added to this solution in an amount according to the desired molar ratio NHDC:gamma-cyclodextrin in the complex.

The mixture is generally stirred until complete dissolution, typically during a period of time comprised between 10 minutes and 3 hours, at a temperature generally comprised between 20° C. and 60° C., preferably comprised between 20° C. and 25° C.

For isolating the solid complex, the solvent is removed by any suitable method, for example, by freeze-drying, or may be evaporated under reduced pressure.

The molar ratio NHDC:gamma-cyclodextrin in the sweetening composition of the present invention is generally comprised between 1.5:1 and 1:10, preferably comprised between 1.5:1 and 1:6, more preferably comprised between 1.2:1 and 1:4, even more preferably comprised between 1.1:1 and 1:3.5 and still more preferably comprised between 1:1 and 1:3.

In a preferred embodiment of the present invention, the molar ratio NHDC:gamma-cyclodextrin is about 1:1.

In another preferred embodiment, the molar ratio NHDC:gamma-cyclodextrin is about 1:3.

The compositions of the present invention provide an outstanding synergistic effect so, surprisingly, gamma-cyclodextrin strongly enhances the sweetness of NHDC. Thus, for example, as disclosed in Example 3 (Table 3), in a sensory test performed with a calibrated panel, it was observed that 5 ppm of NHDC are needed for achieving a sweetness level equivalent to a 1% solution of sucrose in water, when NHDC is used alone. Conversely, when it is used in combination with gamma-cyclodextrin, significantly lower amounts of NHDC are required for achieving the same effect (only 3.5-3.9 ppm in Ex. A-E). Analogously, 24 ppm of NHDC are needed for achieving a sweetness level equivalent to a 3% solution of sucrose in water, when NHDC is used alone, whereas when it is used in combination with gamma-cyclodextrin again significantly lower amounts of NHDC are required (only 12.2-13.5 ppm in Ex. A-E).

Furthermore, surprisingly, for compositions comprising beta-cyclodextrin, instead of gamma-cyclodextrin, exactly the opposite effect is observed (see Comparative Examples A and B in Table 3), i.e., larger amounts of NHDC are needed, regarding using NHDC alone, for achieving the same sweetness level (e.g., 6.1 ppm and 7.7 ppm of NHDC in the composition vs. 5 ppm of NHDC alone, for obtaining 1% sucrose sweetness level; and 28.8 ppm and 28.3 ppm of NHDC in the composition versus 24 ppm of NHDC alone, for achieving 3% sucrose sweetness level).

Figure 2:
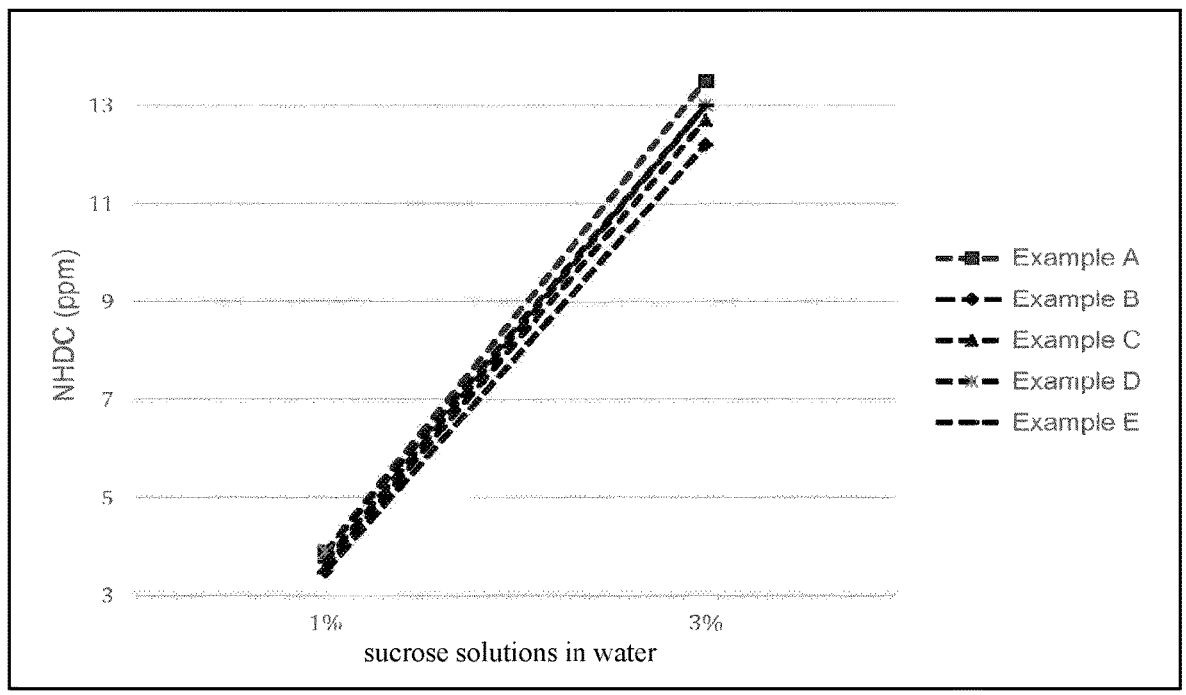
FIG. 2 is a magnified section of the plot displayed in FIG. 1, which further represents the concentrations of neohesperidin dihydrochalcone (NHDC) in combination with gamma-cyclodextrin which are equisweet to 1% and 3% sucrose solutions in water, in a molar ratio NHDC:gamma-cyclodextrin 1:1 (Example A, squares), 1:3 (Example B, diamonds), 1.5:1 (Example C, triangles), 1:6 (Example D, crosses) and 1:10 (Example E, straight line; partial overlapping with the line corresponding to Example D).

The strong sweetness synergy obtained with the sweetening composition of the present invention, comprising gamma-cyclodextrin and NHDC, can be also observed in the graphs of FIGS. 1 and 2.

Furthermore, a quantitative calculation of this synergistic effect is also provided (Example 3, Tables 5 and 6). It can be observed that the compositions of the present invention show notable sweetness synergy, namely, higher than 15% for a 1% sucrose sweetness level, preferably in the range 18% to 40% for a 1% sucrose sweetness level, particularly 29.9% and 38.9% for 1% sucrose sweetness level for a composition having 1:1 and 1:3 molar ratio of NHDC to gamma-cyclodextrin, respectively; and a sweetness synergy higher than 60% for 3% sucrose sweetness level, preferably in the range 60% to 95%, particularly 76.5% and 92.3% of sweetness synergy for 3% sucrose sweetness level, for a composition having 1:1 and 1:3 molar ratio of NHDC to gamma-cyclodextrin, respectively. Conversely, the compositions of the comparative examples, containing beta-cyclodextrin, show negative synergies, i.e., the combination shows a suppressive sweetness effect.

This suppressive effect of beta-cyclodextrin on the sweetness of NHDC is in accordance to the prior art, as disclosed, for example, in the article Chung H. J., *The effect of β-cyclodextrin on the taste quality of neohesperidin dihydrochalcone*, J. Food Sci. Nutr., 1996, 1(2), 186-189.

Another quality of the sweetening compositions of the present invention is that its relative sweetening power decreases less pronouncedly with increasing sweetness levels, compared to NHDC alone.

The relative sweetening power of a given compound, at a given sweetness level, indicates how many times sweeter this compound is than sucrose and it can be calculated as the ratio between the concentration of sucrose and the equisweet concentration of the compound.

A test to evaluate the evolution of the relative sweetening power of the compositions of the present invention was performed (Example 4). The results show (Table 7) that, whereas with NHDC alone the sweetening power relative to sucrose decreases quickly with the sweetness level, the sweetening power of the sweetening compositions of the present invention shows a remarkably slower decrease. This effect can be better appreciated in FIG. 3.

Another advantage of the sweetening composition of the present invention is that it provides an overall taste profile which is closer to sucrose than the taste profile of NHDC alone. The taste profiles of sucrose, NHDC and two compositions according to the present invention were tested (Example 5) by using each sample at concentrations equisweet to 3% sucrose. The following sensory parameters were evaluated on a 0-5 point scale by a calibrated taste panel: time to first sweetness (or onset period, i.e., the time period preceding sweetness onset), time to maximum sweetness (i.e., the time period preceding the maximum sweetness perception), lingering time (i.e., the time period for the sweetness to disappear), menthol/liquorice off-flavour (i.e., the perception of any taste different from sweetness, namely menthol and/or liquorice tastes) and mouthfeel (described as density, i.e., the perceived viscosity in the mouth).

The results obtained, as listed in Table 8 of Example 5, show that the taste profile of NHDC is notably different from the target profile of sucrose, having larger times to first sweetness detection and to reach the maximum sweetness, the lingering is also longer, it is associated to remarkable off-flavours and the mouthfeel is lower.

Conversely, the sweetening agent of the present invention has a taste profile which is closer to the taste profile of sucrose. Thus, compared to NHDC, the times to first and maximum sweetness are reduced, the lingering and off-flavours are also reduced, while the mouthfeel is improved.

Figure 4:
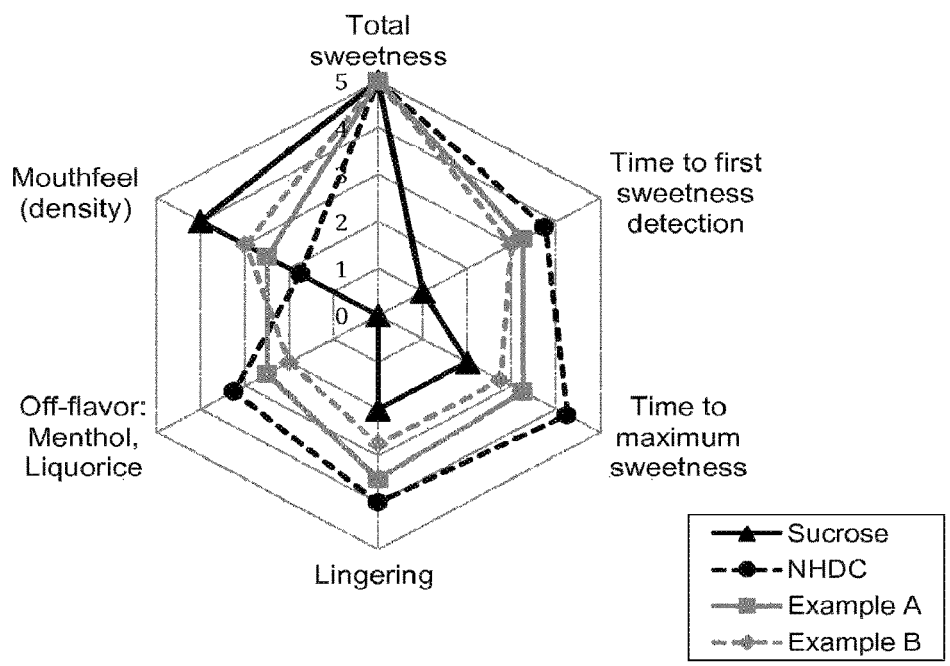
FIG. 4 is a spider diagram representing the organoleptic profile of sucrose (triangles), neohesperidin dihydrochalcone (NHDC, circles) and two compositions comprising NHDC and gamma-cyclodextrin in a molar ratio NHDC:gamma-cyclodextrin 1:1 (Example A, squares) and 1:3 (Example B, diamonds). The sensory descriptors evaluated were total sweetness, time to first sweetness detection, time to maximum sweetness, menthol/liquorice off-flavor and mouthfeel, on a 0-5 point scale.

FIG. 4 shows the results of this comparative taste assay in the form of a spider graph. This graph clearly illustrates how gamma-cyclodextrin brings the taste profile of NHDC closer to that of sucrose. The best results in terms of taste profile are obtained with Example B, which contains a molar ratio NHDC:gamma-cyclodextrin 1:3.

Use as Sweetening Agent

Due to the sweetening synergy observed and to the improved overall taste profile provided, the sweetening composition of the present invention is particularly suitable for sweetening all kind of ingestible products.

Therefore, in a further aspect, the present invention relates to the use of the above defined composition for sweetening an ingestible product.

In a further aspect, the present invention relates to a method of sweetening an ingestible product comprising the step of adding the above defined sweetening composition to the ingestible product. Typically, an effective amount of the sweetening composition is added.

The term "ingestible product", within the meaning of the present invention, relates broadly to any sweetenable substance aimed to be orally ingested, either by a human or by an animal, and includes substances which are drunk, eaten, swallowed or otherwise ingested, namely, food and pharmaceuticals. Furthermore, the term "ingestible product" is meant to include also substances which are not intended to be ingested, but first taken into the mouth and subsequently expelled, for example, chewing gums and oral care compositions, such as mouthwashes, tooth pastes, or tooth gels, for example.

In one embodiment of the present invention, the ingestible product is selected from the group consisting of food products, pharmaceuticals, and oral care compositions; preferably selected from food products and pharmaceuticals.

In another embodiment of the present invention, the ingestible product is a food product.

In another embodiment of the present invention, the ingestible product is a pharmaceutical product.

The expression "food product", as used herein, means any edible product intended for human or animal nutrition, and includes solids, semi-solids and liquids, including also beverages. The expression "food product" also includes products which are intended to be only partially ingested and subsequently expelled from the oral cavity, particularly, chewing gums.

The beverages suitable to be sweetened with the composition of the present invention can be, without limitation, any kind of sweetenable beverage, either carbonated or non-carbonated, either alcoholic or non-alcoholic, and include, among others, fruit-flavoured soft drinks, sodas, colas, sport drinks, and, in general, any drink containing and/or flavoured with fruits, vegetables, aromatic plants, tea, coffee or cocoa, for example; it also includes beverages containing wine or beer, for example. The beverage category includes those beverages ready to drink, as well as other forms, like powders, granulates, tablets or liquid concentrates, which are intended to be reconstituted with water.

Other food products are, for example, bakery products, such as bread, cakes, biscuits, muffins, and, in general, any kind of baked food; also dairy products such as yogurt, drinkable yogurt, frozen yogurt, milk, milk-based beverages, condensed milk, cream, cheese or ice cream; soy-based products, such as soy milk or soy-lecithin; confectionary products, such as chocolate, caramels, candies, marzipan, or chewing gums; cereal-type products, such as breakfast cereals, cereal bars, energy/nutritional bars or flakes; fruit derived products, such as jam, fruit purees, preserved fruits, or sauces; vegetable derived products, such as sauces, dried vegetables, preserved vegetables or frozen vegetables; oil based products and emulsions, such as mayonnaise and several dressings; among many others.

The food product category also includes, in particular, nutritional or dietary supplements, i.e., food products which are enriched in some nutritional ingredients, for example, vitamins, minerals, amino acids, proteins, botanicals, enzymes or other substances intended to supplement the human diet, and which may be in any suitable food form, typically, as beverages or bars, for example.

Also included into the food product expression are any kinds of dried products, such as dessert mixes or dried ready meals.

The food products also include, in particular, any feed intended for animal nutrition.

The pharmaceutical products suitable to be sweetened with the composition according to the present invention include formulations containing any drug for oral administration, either for human or veterinary therapy, and include any kind of health supplement as well, for example, vitamins, minerals and mixtures thereof. The pharmaceutical products can be in any form suitable for oral administration, as are well known to the skilled in the art, for example solid forms, such as tablets, chewable tablets, orally disintegrating tablets (ODT), sub-lingual tablets, orally disintegrating films (flash films), lozenges, chewable gums or powders; or liquid forms, such as drops, syrups or suspensions; or alternatively, in the form of powders, granulates, or tablets intended to be dissolved in a liquid to be administered, for example, effervescent tablets.

It is understood that the above examples are non-limiting and any ingestible product which is suitable to be sweetened may be appropriate to be sweetened using the composition of the present invention.

The term "sweetening" as used herein, relates to the common meaning of this term, i.e., providing sweet taste to an edible product. Such sweetening effect is understood to encompass embodiments wherein the sweetening composition is the only source of sweetness present in the product, as well as other alternative embodiments wherein it is used in combination with other sweeteners.

Therefore, in one embodiment, the sweetening composition of the present invention is used in combination with other sweetening agents, for example, with other high-intensity sweeteners (low-calorie sweeteners), such as stevia extracts, monk fruit, acesulfame K, aspartame, cyclamate, neotame, saccharin, sucralose, thaumatin, or mixtures thereof; and/or with carbohydrate sweeteners (caloric sweeteners) such as sucrose, glucose, fructose, and mixtures thereof.

When the sweetened edible product is a food product, particularly for human consumption, the sweetening composition is generally used in combination with a carbohydrate sweetener. In this particular embodiment, the composition is used as a sugar substitute or sugar reducing agent and it has the purpose of reducing as much as possible the amount of sugar contained in the food product, without altering the sugar-like taste of the product. Indeed, the sweet taste provided by carbohydrate sweeteners is generally the best accepted by consumers, while, in general, the taste profiles of high-intensity sweeteners are not able to fully emulate the sugar taste, namely due to their different onset, duration, mouthfeel and/or aftertastes.

Surprisingly, it was found that the use of the composition of the present invention allows reducing the amount of NHDC required for replacing a certain proportion of sugar in an ingestible product, namely, in a food product. Thus, for example, as disclosed in Example 6, the present composition was used for sweetening an orange soft drink, for replacing part of the content of the high fructose corn syrup (HFCS) originally used as sweetener. It was found that, using NHDC alone, the maximum sugar reduction achieved, without any taste change being perceived by a calibrated panel, was 10% reduction of the HFCS, by using 10 ppm of NHDC as a replacer. However, when a composition comprising NHDC and gamma-cyclodextrin according to the present invention was used, the same percentage of sugar replacement was achieved with only 4.5 ppm of NHDC, also without any change in the overall taste profile.

Additionally, the present composition is also effective for increasing the proportion of sugar which can be replaced in a sweetened edible product, without any perceivable change in the taste profile. Thus, for example, as disclosed in Example 7, using NHDC alone as sugar substitute, it was possible a 15% sucrose reduction in an orange juice based soft drink, while, by using the combination of NHDC and gamma-cyclodextrin, it was possible to reduce the sugar content up to a 25%. Analogously, as disclosed in Example 8, using NHDC alone as sugar substitute, it was possible a 10% reduction of the sugar content in a dark chocolate product; however, when the composition of the invention was used as a sugar substitute, it was possible to reduce the sugar content of the chocolate product up to the 28%.

Therefore, the composition of the present invention, comprising NHDC and gamma-cyclodextrin improves the sugar-replacing efficiency of NHDC, i.e., for a given proportion of sugar to be replaced, it allows using less amount of NHDC and, moreover, it also allows replacing larger proportions of sugar in an edible product without any perceivable taste variation than when using NHDC alone.

In an embodiment of the invention, the sweetening composition is used as a sugar replacing agent. As used herein, sugar is meant to embrace any suitable carbohydrate sweetener, for example, sucrose, glucose, fructose, and mixtures thereof.

The percentage of sugar which is replaced with the sweetening agent varies depending on the particular food product. For example, the percentage of carbohydrate sweetener replaced is typically in the range 5-60%, preferably in the range 10-30%, wherein the percentage relates to the weight of carbohydrate sweetener replaced regarding the total original carbohydrate content.

Typically, the use of the composition for sweetening an ingestible product involves adding the composition to the ingestible product.

The sweetening composition of the invention can be added to the ingestible product in a conventional way, analogously to usual sweetening agents. For example, it may be added to a pharmaceutical product together with other pharmaceutical excipients, or it may be added to food products, by incorporating it at some stage of the manufacturing process, as is well known to the skilled person in pharmaceutical technology or food technology.

In an alternative embodiment, the sweetening composition may be generated in situ, so both components, i.e., NHDC and gamma-cyclodextrin may be added separately, preferably consecutively, during the manufacture of the ingestible product, typically followed by thoroughly mixing.

In a further aspect, the present invention relates to a process for sweetening an ingestible product comprising adding the above defined sweetening composition to the ingestible product.

In a further aspect, the present invention also relates to a sweetened ingestible product comprising the above defined sweetening composition.

The amount of the sweetening composition used for sweetening the ingestible product, or included in the sweetened ingestible product is meant to be an "effective amount" for sweetening it, i.e., for providing sweet taste to the ingestible product. This "effective amount" varies widely depending on the particular product and depending also on the degree of sweetness desired. The skilled in the art can readily establish the appropriate amount of the composition to be added to the ingestible product, depending on the particular case.

For example, the amount of the sweetening composition used for sweetening the ingestible product, or contained in the sweetened ingestible product, can be in the range 1-5000 ppm, preferably in the range 1-500 ppm, more preferably in the range 1-200 ppm, relative to the total weight of the ingestible product. The total weight of the ingestible product is meant to include also the weight of the added sweetening composition.

The aspects of the present invention related to the sweetening composition comprising NHDC and gamma-cyclodextrin can be defined according to the following embodiments:

1.—Sweetening composition comprising neohesperidin dihydrochalcone and gamma-cyclodextrin.
2.—Sweetening composition according to embodiment 1, characterized in that it is a mixture of neohesperidin dihydrochalcone and gamma-cyclodextrin.
3.—Sweetening composition according to embodiment 1, characterized in that neohesperidin dihydrochalcone and gamma-cyclodextrin are in the form of a complex.
4.—Sweetening composition according to any one of embodiments 1 to 3, characterized in that the molar ratio neohesperidin dihydrochalcone:gamma-cyclodextrin is comprised between 1.5:1 and 1:10.
5.—Composition according to any one of embodiments 1 to 4, characterized in that the molar ratio neohesperidin dihydrochalcone:gamma-cyclodextrin is comprised between 1.5:1 and 1:6.
6.—Composition according to embodiment 5, characterized in that the molar ratio neohesperidin dihydrochalcone:gamma-cyclodextrin is comprised between 1.2:1 and 1:4.
7.—Composition according to embodiment 6, characterized in that the molar ratio neohesperidin dihydrochalcone:gamma-cyclodextrin is comprised between 1.1:1 and 1:3.5.
8.—Composition according to embodiment 7, characterized in that the molar ratio neohesperidin dihydrochalcone:gamma-cyclodextrin is comprised between 1:1 and 1:3.
9.—Composition according to any one of embodiments 1 to 8, characterized in that the molar ratio neohesperidin dihydrochalcone:gamma-cyclodextrin is about 1:1.
10.—Composition according to any one of embodiments 1 to 8, characterized in that the molar ratio neohesperidin dihydrochalcone:gamma-cyclodextrin is 1±0.1:1±0.1.
11.—Composition according to embodiment 10, characterized in that the molar ratio neohesperidin dihydrochalcone:gamma-cyclodextrin is 1±0.05:1±0.05.
12.—Composition according to any one of embodiments 1 to 11, characterized in that the molar ratio neohesperidin dihydrochalcone:gamma-cyclodextrin is 1:1.
13.—Composition according to any one of embodiments 1 to 8, characterized in that the molar ratio neohesperidin dihydrochalcone:gamma-cyclodextrin is about 1:3.
14.—Composition according to any one of embodiments 1 to 8, characterized in that the molar ratio neohesperidin dihydrochalcone:gamma-cyclodextrin is 1±0.1:3±0.3.
15.—Composition according to embodiment 14, characterized in that the molar ratio neohesperidin dihydrochalcone:gamma-cyclodextrin is 1±0.05:3±0.15.
16.—Composition according to any one of embodiments 1 to 15, characterized in that the molar ratio neohesperidin dihydrochalcone:gamma-cyclodextrin is 1:3.
17.—Use of the composition according to any one of embodiments 1 to 16 for sweetening an ingestible product.
18.—Use according to embodiment 17, characterized in that the ingestible product is selected from a food product and a pharmaceutical product.
19.—Use according to embodiment 17 or 18, characterized in that the ingestible product is a food product.
20.—Use according to embodiment 19, characterized in that the food product is for human nutrition.
21.—Use according to embodiment 19, characterized in that the food product is for animal nutrition.
22.—Use according to embodiment 19, characterized in that the food product is a beverage.
23.—Use according to embodiment 19, characterized in that the composition is used as a sugar replacing agent.
24.—Use according to any one of embodiments 17 to 23, characterized in that the composition is administered in combination with at least one further sweetening agent.

25.—Use according to embodiment 24, characterized in that the at least one further sweetening agent is selected from the group consisting of stevia extracts, monk fruit, acesulfame K, aspartame, cyclamate, neotame, saccharin, sucralose, thaumatin, sucrose, glucose, fructose and mixtures thereof.

26.—Process for sweetening an ingestible product comprising adding the sweetening composition of any one of embodiments 1 to 16 to the ingestible product.

27.—Process according to embodiment 26, characterized in that the sweetening composition is generated in situ.

28.—Process according to embodiment 27, wherein each component of the sweetening composition is added separately during the manufacture of the ingestible product, preferably each component of the sweetening composition is added consecutively during the manufacture of the ingestible product.

29.—Process according to any one of embodiments 26 to 28, characterized in that the sweetening composition is added in an amount comprised between 1 and 5000 ppm, preferably comprised between 1 and 500 ppm, and more preferably comprised between 1 and 200 ppm, relative to the total weight of the ingestible product.

30.—Process according to any one of embodiments 26 to 29, characterized in that the ingestible product is selected from a food product and a pharmaceutical product.

31.—Process according to embodiment 30, characterized in that the ingestible product is a food product.

32.—Process according to embodiment 31, characterized in that the food product is for human nutrition.

33.—Process according to embodiment 31, characterized in that the food product is for animal nutrition.

34.—Process according to embodiment 31, characterized in that the food product is a beverage.

35.—Ingestible product comprising the sweetening composition according to any one of embodiments 1 to 16.

36.—Ingestible product according to embodiment 35, characterized in that the sweetening composition is in an amount comprised between 1 and 5000 ppm, preferably comprised between 1 and 500 ppm, and more preferably comprised between 1 and 200 ppm, relative to the total weight of the ingestible product.

37.—Ingestible product according to embodiment 35 or 36, characterized in that the ingestible product is selected from a food product and a pharmaceutical product.

38.—Ingestible product according to embodiment 37, characterized in that the ingestible product is a food product.

39.—Ingestible product according to embodiment 38, characterized in that the food product is for human nutrition.

40.—Ingestible product according to embodiment 38, characterized in that the food product is for animal nutrition.

41.—Ingestible product according to embodiment 38, characterized in that the food product is a beverage.

Taste-Masking Agent

Another aspect of the invention is the use of a composition comprising neohesperidin dihydrochalcone and a cyclodextrin selected from beta-cyclodextrin and gamma-cyclodextrin as taste-masking agent.

In one embodiment of the invention, the taste-masking composition is a mixture of NHDC and the beta- or gamma-cyclodextrin, and can be prepared by simple dry blending of both components using any suitable blending means, for example, using a tumbling mixer or agitator mixer.

In another embodiment of the invention, the taste-masking composition is in the form of a complex.

In this complex, NHDC is presumably inserted, at least partially, into the cavity of the beta- or the gamma-cyclodextrin, forming an inclusion complex. However, the term "complex", within the meaning of the present invention, is meant to include other possible variations, involving further non-stoichiometric interactions between NHDC and the cyclodextrin to form the supramolecular complex.

This complex is typically prepared by dissolving the cyclodextrin in a suitable solvent, preferably in water, and subsequently adding NHDC to the solution and isolating the complex from the solution.

For preparing the complex with gamma-cyclodextrin, the concentration of gamma-cyclodextrin in the solution is generally comprised between 1-20% w/v, preferably between 5-10% w/v. For preparing the complex with beta-cyclodextrin, the concentration of beta-cyclodextrin in the solution is generally comprised between 0.5-5% w/v, preferably between 1-2% w/v.

The NHDC is added to cyclodextrin solution in an amount according to the desired molar ratio NHDC:cyclodextrin in the complex.

The mixture obtained is generally stirred until completely dissolution, typically during a period of time comprised between 10 minutes and 3 hours, at a temperature generally comprised between 20° C. and 60° C.

For isolating the solid complex, the solvent is removed by any suitable method, for example, by freeze-drying, or may be evaporated under reduced pressure.

As used herein, taste-masking agent, or taste masker, means any substance or composition providing a taste-masking effect. A taste-masking effect, as is well known in the art, means the perceived reduction, modulation, or elimination of an unpleasant taste or unpleasant taste impression of a substance.

Typically, for exerting the taste-masking effect, the taste-masking composition is mixed with the unpleasantly tasting substance, generally, both contained in an edible product.

In a further aspect, the present invention relates to a method of masking the unpleasant taste of a substance comprising the step of adding a composition comprising neohesperidin dihydrochalcone and a cyclodextrin selected from beta-cyclodextrin and gamma-cyclodextrin to the unpleasantly tasting substance. Typically, the composition comprising neohesperidin dihydrochalcone and the cyclodextrin is added to the unpleasantly tasting substance in a taste-masking effective amount.

Alternatively, the taste-masking composition can be prepared in situ, so both components, i.e., NHDC and the beta- or gamma-cyclodextrin, may be added separately, preferably consecutively, to an unpleasantly tasting substance or to an ingestible product comprising an unpleasantly tasting substance, typically followed by thoroughly mixing.

As shown, in Examples 10-12, it was surprisingly found that compositions comprising the composition comprising NHDC and beta-cyclodextrin or gamma-cyclodextrin show strong taste-masking synergy, that is to say, the taste-masking effect achieved with the combination components is higher than the sum of the effects of each individual substance.

This synergic effect results in considerable cost savings, since it allows using less amount of substances for masking unpleasant tastes in ingestible products, namely, in food products and pharmaceuticals.

Unpleasant tasting substances for the purposes of the invention are: a) substances which taste bitter, astringent, cardboardy, dusty, floury, rancid and/or metallic and, b) substances that have a bitter, astringent, cardboardy, dusty, dry, floury, rancid or metallic aftertaste.

Among the unpleasant tastes or unpleasant taste impressions which can be masked according to the use of the present invention are, for example, bitterness, astringency and metallic tastes, preferably bitterness and/or astringency.

In one embodiment, the taste-masking agent according to the present invention is used for masking an unpleasant taste which is selected from bitterness and astringency, or a mixture of bitterness and astringency.

When used specifically for masking bitterness, the taste-masking agent or taste masker may be referred to as anti-bittering agent, or bitter-masking agent.

When used specifically for masking astringency, the taste-masking agent or taste masker may be referred to as antiastringency agent, or astringency-masking agent.

The molar ratio NHDC:cyclodextrin in the taste-masking composition of the present invention is generally comprised between 1.5:1 and 1:6, preferably comprised between 1.2:1 and 1:4 and more preferably comprised between 1.1:1 and 1:3.5 and still more preferably comprised between 1:1 and 1:3.

In a preferred embodiment, the molar ratio NHDC:cyclodextrin is about 1:1.

In another preferred embodiment, the molar ratio NHDC:cyclodextrin is about 1:3.

In one embodiment of the invention, the cyclodextrin is gamma-cyclodextrin.

In another embodiment of the invention, the cyclodextrin is beta-cyclodextrin.

The bitter taste or bitterness is believed to be produced by certain substances which bind to special bitter taste receptors, located on the apical membrane of the taste receptor cells located in the taste buds on the tongue. The bitterness receptors are believed to be members of the G protein-coupled receptor (GPCR) superfamily, and are referred to as T2Rs. These bitter receptors are able to interact with ligands which are chemically very diverse, so there is a large number of substances which are described as bitter, whose chemical structures may belong to many different chemical classes.

In general, the taste of any substance known to impart a bitter taste may be masked using the composition according to the present invention, i.e., using the combination of NHDC and beta- or gamma-cyclodextrin.

A non-limiting list of bitter substances includes, for example, flavanones, such as naringin, neohesperidin or hesperidin; flavones such as tangeritin or nobiletin; flavonols, such as avicularin, quercetin, quercitrin, isoquercetin, myricetin, or rutin; flavanols, such as taxifolin, catechins (catechin, epicatechin, epicatechin gallate, epigallocatechin, or epigallocatechin gallate) or theaflavins (theaflavin, isotheaflavin, neotheaflavin, theaflavin-3-gallate, theaflavin-3'-gallate, theaflavin-3,3'-digallate, isotheaflavin-3-gallate or theaflavic acid); isoflavones, such as genistein or daidzein; chalcones, such as phloridzin, triterpenes, such as limonin, nomilin or limonin glucoside; hydroxycinnamic acids such as caffeic acid or esters thereof; olive polyphenols such as oleuropein, glucosinolates, such as sinigrin, progoitrin or glucobrassicin; alkaloids, such as nicotine, theobromine, theophylline, quinine or caffeine; phenolic glycosides, such as salicin or arbutin; bitter alpha-acids found in the resin of hops, such as humulone, adhumulone, cohumulone, posthumulone, or prehumulone; metal salts, in particular potassium, magnesium and bismuth salts, such as potassium chloride, potassium gluconate, potassium carbonate, potassium succinate, potassium lactate, potassium malate; bismuth subcitrate, bismuth citrate, bismuth subgalate, bismuth salicylate or magnesium sulfate; some pharmaceutical active ingredients, such as fluoro-quinolone antibiotics, aspirin, ibuprofen, paracetamol, dextromethorphan, phenylephrine, loperamide, tramadol, ranitidine hydrochloride, acetylcysteine, glucosamine sulfate, erythromycin, levosulpiride, chlorhexidine, diosmin, β-lactam antibiotics, ambroxol, or guaifenesin; unsaturated fatty acids; vitamins; bitter tasting amino acids (e.g. leucine, isoleucine, valine, tryptophan, proline, histidine, tyrosine, lysine or phenylalanine) and some bitter-tasting peptides, particularly those containing the hydrophobic amino acids phenylalanine, tyrosine, tryptophan, leucine, isoleucine and valine.

Astringency is defined by the American Society for Testing and Materials (ASTM, 2004) as the complex of sensations due to shirking, drawing or puckering of the epithelium as a result of exposure to substances such as alums and tannins. It is believed that astringent molecules react with salivary proteins, especially proline-rich proteins, causing them to precipitate, and the resulting loss of lubricity leads to the tactile feeling associated with astringency in the mouth.

Astringent molecules are commonly plant-based products, most commonly tannins, present in fruits and leaves or bark.

Some substances typically perceived as astringent are, for example, tea, red wine, rhubarb and unripe persimmons and bananas.

A typical example of substance providing astringent impression is green tea, which contains several polyphenols, known as catechins, which are known to be astringent, namely, catechin, epigallocatechin gallate, epigallocatechin, epicatechin gallate, epicatechin and their respective stereoisomers. Other examples of substances that cause astringency are proteins, such as pea protein, whey protein and soy protein.

Another example of astringent taste substances are the theaflavins of black tea, namely, theaflavin, theaflavin-3-gallate, theaflavin-3'-gallate, theaflavin-3,3'-digallate, and theaflavic acid.

The taste of some substances may be perceived as a mixture of bitterness and astringency. Thus, for example, the astringent taste of green tea and black tea is sometimes perceived as a mixture of bitterness/astringency.

Other substances may have a primary taste or flavour which is not unpleasant, but have an additional unpleasant taste like bitterness, astringency or metallic notes. Without limitation, these substances may belong to the group comprising aspartame, neotame, superaspartame, saccharin, sucralose, tagatose, monellin, monk fruit, stevia extracts, individual steviol glycosides or their combinations, hernandulcin, thaumatin, miraculin, glycyrrhizin, glycyrrhetinic acid and cyclamate.

In one embodiment, the composition comprising NHDC and gamma- or beta-cyclodextrin, according to the present invention, is used as antibittering agent.

In another embodiment, the composition comprising NHDC and gamma- or beta-cyclodextrin, according to the present invention, is used as antiastringency agent.

Preferably, the composition is used for masking the bitterness and/or astringency of a substance selected from the group consisting of: caffeine, ibuprofen, limonin, naringin, paracetamol, aspirin, potassium chloride, quercetin, quinine, theobromine, catechin, epigallocatechin gallate, epigallocatechin, epicatechin gallate, epicatechin, dextromethorphan, phenylephrine, guaifenesin, bismuth subsalicylate, soy protein, whey protein, pea protein, aspartame, sucralose, saccharin, stevia extracts and mixtures thereof.

More preferably, the composition is used for masking the bitterness and/or astringency of a substance selected from the group consisting of caffeine, naringin, paracetamol, potassium chloride, proteins, catechins, sucralose, stevia extracts and mixtures thereof.

In a preferred embodiment, the taste-masking composition is used for masking the bitterness of paracetamol. Preferably, a composition comprising NHDC and gamma-cyclodextrin is used. According to this embodiment, the molar ratio NHDC:gamma cyclodextrin is preferably comprised between 1.5:1 and 1:10, more preferably comprised between 1.5:1 and 1:6, even more preferably comprised between 1.2:1 and 1:4, still more preferably comprised between 1.1:1 and 1:3.5 and still more preferably comprised between 1:1 and 1:3. In a particularly preferred embodiment the ratio is about 1:3. In another particularly preferred embodiment, the ratio is about 1:1.

In another preferred embodiment, the taste-masking composition is used for masking the bitterness of quinine. Preferably, a composition comprising NHDC and beta-cyclodextrin is used. According to this embodiment, the molar ratio NHDC:beta cyclodextrin is preferably comprised between 1.5:1 and 1:10, more preferably comprised between 1.5:1 and 1:6, even more preferably comprised between 1.2:1 and 1:4, still more preferably comprised between 1.1:1 and 1:3.5 and still more preferably comprised between 1:1 and 1:3. In a particularly preferred embodiment the ratio is about 1:3. In another particularly preferred embodiment, the ratio is about 1:1.

In another preferred embodiment, the taste-masking composition is used for masking the astringent taste of green tea. According to this embodiment, the composition has astringency masking effect against the astringent components of green tea, typically, the catechins epigallocatechin gallate, epigallocatechin, epicatechin gallate and/or epicatechin.

According to this embodiment, the molar ratio NHDC:cyclodextrin is preferably comprised between 1.5:1 and 1:10, more preferably comprised between 1.5:1 and 1:6, even more preferably comprised between 1.2:1 and 1:4, still more preferably comprised between 1.1:1 and 1:3.5 and still more preferably comprised between 1:1 and 1:3. In a particularly preferred embodiment the ratio is about 1:3. In another particularly preferred embodiment, the ratio is about 1:1.

The taste-masking agent according to the present invention is typically added to an ingestible product which comprises an unpleasantly tasting substance, typically, which comprises a bitter substance and/or an astringent substance.

Another aspect of the invention is a process for masking the unpleasant taste of an ingestible product which contains at least one unpleasantly tasting substance comprising adding to the ingestible product a taste-masking composition comprising neohesperidin dihydrochalcone and a cyclodextrin selected from beta-cyclodextrin and gamma-cyclodextrin.

The step of adding the taste-masking composition to the ingestible product is meant to include adding the premixed composition, as well as incorporating both components, i.e., NHDC and the beta- or gamma-cyclodextrin, separately, preferably consecutively, to the ingestible product.

Another aspect of the invention is an ingestible product which comprises at least one unpleasantly tasting substance and a taste-masking composition comprising neohesperidin dihydrochalcone and a cyclodextrin selected from beta-cyclodextrin and gamma-cyclodextrin. Preferably, the unpleasantly tasting substance is a bitter or an astringent substance.

The amount of the unpleasantly tasting substance contained in the ingestible product is sufficient to be perceived as unpleasant when the ingestible product does not comprise the taste-masking agent.

In one embodiment, the amount of the unpleasantly tasting substance in the ingestible product is in the range 1-5000 ppm, based on the total weight of the ingestible product, without taste-masking agent.

The taste-masking agent is added to the ingestible product in a taste-masking effective amount. As used herein, a "taste-masking effective amount" is the amount of the taste-masking composition that is sufficient to reduce, modify or eliminate the unpleasant taste of the unpleasantly tasting substance as compared to the ingestible product without the taste-masking agent. The taste masking effective amount may vary widely depending on the particular unpleasantly tasting substance, on its relative amount in the ingestible product, and on the particular ingestible product.

The skilled in the art will have no difficulty in choosing the appropriate amount of the taste-masker in each particular case.

In one embodiment, the taste-masking composition is added in an amount comprised between 1-2000 ppm, preferably comprised between 1-1000 ppm, and more preferably comprised between 1-500 ppm, relative to the total weight of the ingestible product. The total weight of the ingestible product is meant to include also the weight of the added sweetening composition.

The term "ingestible product", as used herein, relates broadly to any substance aimed to be orally ingested, either by a human or by an animal, and includes substances which are drunk, eaten, swallowed or otherwise ingested, namely, food products and pharmaceuticals. Furthermore, the term "ingestible product" is meant to include also substances which are not intended to be ingested, but first taken into the mouth and subsequently expelled, for example, chewing gums and oral care compositions, such as mouthwashes, tooth pastes, or tooth gels, for example.

In one embodiment of the present invention, the ingestible product is selected from the group consisting of food products, pharmaceuticals, and oral care compositions; preferably selected from food products and pharmaceuticals.

In another embodiment of the present invention, the ingestible product is a food product.

In another embodiment of the present invention, the ingestible product is a pharmaceutical product.

The expression "food product", as used herein, means any edible product intended for human or animal nutrition, and includes solids, semi-solids and liquids, including also beverages. The expression "food product" also includes products which are intended to be only partially ingested and subsequently expelled from the oral cavity, particularly, chewing gums.

The beverages suitable to add therein the taste-masking agent according to the present invention can be, without limitation, any kind of beverage containing an unpleasantly tasting substance, preferably, containing a bitter and/or astringent substance, and they may be either carbonated or non-carbonated, either alcoholic or non-alcoholic, and include, among others, fruit-flavoured soft drinks, sodas, colas, sport drinks, and, in general, any drink containing and/or flavoured with fruits, vegetables, aromatic plants, tea, coffee or cocoa, for example; it also includes beverages containing wine or beer, for example; it also includes energy or healthy drinks containing, for example, protein hydrolysates, vitamins and/or phytonutrients having bitter and/or astringent tastes.

The beverage category includes those beverages ready to drink, as well as other forms, like powders, granulates, tablets or liquid concentrates, which are intended to be reconstituted with water.

Other food products suitable to add therein the taste-masking agent according to the present invention are, for example, bakery products, such as bread, cakes, biscuits, muffins, and, in general, any kind of baked food; also dairy products such as yogurt, drinkable yogurt, frozen yogurt, milk, milk-based beverages, condensed milk, cream, cheese or ice cream; soy-based products, such as soy milk or soy-lecithin; confectionary products, such as chocolate, caramels, candies, marzipan, or chewing gums; cereal-type products, such as breakfast cereals, cereal bars, energy/nutritional bars or flakes; fruit derived products, such as jam, fruit purees, preserved fruits, and sauces; vegetable derived products, such as sauces, dried vegetables, preserved vegetables or frozen vegetables; oil based products and emulsions, such as mayonnaise and several dressings, among many others, provided that they contain an unpleasantly tasting substance, preferably a bitter and/or astringent tasting substance.

The food product category also includes, in particular, nutritional or dietary supplements, i.e., food products which are enriched in some nutritional ingredients, for example, vitamins, minerals, amino acids, proteins, botanicals, enzymes or other substances intended to supplement the human diet, and which may be in any suitable food form, typically as beverages or bars, for example.

Also included into the food product expression are any kinds of dried products, such as desert mixes or dried ready meals.

Food products also include, in particular, any feed intended for animal nutrition.

The pharmaceutical products suitable to add therein the taste-masking agent according to the present invention are those comprising an unpleasantly tasting active ingredient, namely, a bitter or astringent ingredient, including as well any kind of unpleasantly tasting health supplement, for example, vitamins, minerals and mixtures thereof. Preferably, the bitter or astringent active ingredient is selected from fluoro-quinolone antibiotics, ibuprofen, paracetamol, β-lactam antibiotics, ambroxol, guaifenesin, and mixtures thereof; preferably the active ingredient is paracetamol.

The pharmaceutical products can be in any form suitable for oral administration either for human or veterinary therapy. The pharmaceutical products can be in any form suitable for oral administration, as are well known to the skilled in the art, for example solid forms, such as tablets, chewable tablets, orally disintegrating tablets (ODT), sub-lingual tablets, orally disintegrating films (flash films), lozenges, chewable gums, or powders; or liquid forms, such as drops, syrups and suspensions; or alternatively, in the form of powders, granulates, or tablets intended to be dissolved in a liquid to be administered, for example, effervescent tablets.

The taste-masking composition of the invention can be added to the ingestible product in a conventional way, as is well known to the skilled in pharmaceutical technology or food technology, for example, can be added to a pharmaceutical product, together with other excipients of the formulation, or to a food product at a suitable stage of the manufacturing process.

It is understood that the above examples are non-limiting and any ingestible product containing an unpleasantly tasting substance, preferably a bitter and/or astringent substance, may be appropriate to add therein the taste-masking composition according to the present invention.

Another aspect of the invention relates to a taste-masking composition comprising neohesperidin dihydrochalcone and gamma-cyclodextrin.

In one embodiment, the taste-masking composition is a mixture of both components.

In another embodiment, NHDC and gamma-cyclodextrin are in the form of a complex.

The molar ratio NHDC:gamma-cyclodextrin according to this aspect of the invention is generally comprised between 1.5:1 and 1:10, more preferably comprised between 1.5:1 and 1:6, even more preferably comprised between 1.2:1 and 1:4, still more preferably comprised between 1.1:1 and 1:3.5 and still more preferably comprised between 1:1 and 1:3.

In a preferred embodiment of this aspect of the invention, the molar ratio NHDC:gamma-cyclodextrin is about 1:1.

In another preferred embodiment, the molar ratio NHDC:gamma-cyclodextrin is about 1:3.

The aspects of the present invention related to the taste-masking composition comprising NHDC and gamma-cyclodextrin or beta-cyclodextrin can be defined according to the following embodiments:

1.—Use of a composition comprising neohesperidin dihydrochalcone and a cyclodextrin selected from beta-cyclodextrin and gamma-cyclodextrin as taste-masking agent.

2.—Use according to embodiment 1, characterized in the composition is a mixture of neohesperidin dihydrochalcone and the cyclodextrin.

3.—Use according to embodiment 1, characterized in that neohesperidin dihydrochalcone and the cyclodextrin are in the form of a complex.

4.—Use according to any one of embodiments 1 to 3, characterized in that the molar ratio neohesperidin dihydrochalcone:cyclodextrin is comprised between 1.5:1 and 1:10.

5.—Use according to any one of embodiments 1 to 4, characterized in that the molar ratio neohesperidin dihydrochalcone:cyclodextrin is comprised between 1.5:1 and 1:6.

6.—Use according to embodiment 5, characterized in that the molar ratio neohesperidin dihydrochalcone:cyclodextrin is comprised between 1.2:1 and 1:4.

7.—Use according to embodiment 6, characterized in that the molar ratio neohesperidin dihydrochalcone:cyclodextrin is comprised between 1.1:1 and 1:3.5.

8.—Use according to embodiment 7, characterized in that the molar ratio neohesperidin dihydrochalcone:gamma-cyclodextrin is comprised between 1:1 and 1:3.

9.—Use according to any one of embodiments 1 to 8, characterized in that the molar ratio neohesperidin dihydrochalcone:cyclodextrin is 1:1.

10.—Use according to any one of embodiments 1 to 8, characterized in that the molar ratio neohesperidin dihydrochalcone:cyclodextrin is about 1:1.

11.—Use according to any one of embodiments 1 to 8, characterized in that the molar ratio neohesperidin dihydrochalcone:cyclodextrin is 1±0.1:1±0.1.

12.—Use according to embodiment 11, characterized in that the molar ratio neohesperidin dihydrochalcone:cyclodextrin is 1±0.05:1±0.05.

13.—Use according to any one of embodiments 1 to 8, characterized in that the molar ratio neohesperidin dihydrochalcone:cyclodextrin is 1:3.

14.—Use according to any one of embodiments 1 to 8, characterized in that the molar ratio neohesperidin dihydrochalcone:cyclodextrin is about 1:3.

15.—Use according to any one of embodiments 1 to 8, characterized in that the molar ratio neohesperidin dihydrochalcone:cyclodextrin is 1±0.1:3±0.3.

16.—Use according to embodiment 15, characterized in that the molar ratio neohesperidin dihydrochalcone:cyclodextrin is 1±0.05:3±0.15.

17.—Use according to any one of embodiments 1 to 16, characterized in that the cyclodextrin is beta-cyclodextrin.

18.—Use according to any one of embodiments 1 to 16, characterized in that the cyclodextrin is gamma-cyclodextrin.

19.—Use according to any one of embodiments 1 to 18 for masking bitterness.

20.—Use according to any one of embodiments 1 to 19 for masking astringency.

21.—Use according to any one of embodiments 1 to 20 for masking metallic notes.

22.—Use according to any one of embodiments 1 to 21 for masking bitterness and/or astringency and/or metallic notes.

23.—Use according to any one of embodiments 1 to 20 for masking the bitterness and/or astringency of a substance selected from the group consisting of: caffeine, ibuprofen, limonin, naringin, paracetamol, aspirin, potassium chloride, quercetin, quinine, theobromine, catechin, epigallocatechin gallate, epigallocatechin, epicatechin gallate, epicatechin, dextromethorphan, phenylephrine, guaifenesin, bismuth subsalicylate, soy protein, whey protein, pea protein, aspartame, sucralose, saccharin, stevia extracts and mixtures thereof.

24.—Use according to embodiment 23, characterized in that the substance is selected from the group consisting of: caffeine, naringin, paracetamol, potassium chloride, proteins, catechins, sucralose, stevia extracts and mixtures thereof.

25.—Use according to any one of embodiments 1 to 18, characterized in that it is for masking the bitterness of paracetamol.

26.—Use according to any one of embodiments 1 to 18, characterized in that it is for masking the bitterness of quinine.

27.—Use according any one of embodiments 1 to 18, characterized in that it is for masking the astringency of green tea.

28.—Process for masking the unpleasant taste of an ingestible product which contains at least one unpleasantly tasting substance comprising adding to the ingestible product a taste-masking composition comprising neohesperidin dihydrochalcone and a cyclodextrin selected from beta-cyclodextrin and gamma-cyclodextrin.

29.—Process according to embodiment 28, characterized in that the taste-masking composition has a molar ratio neohesperidin dihydrochalcone:cyclodextrin which is comprised between 1.5:1 and 1:10.

30.—Process according to embodiment 28 or 29, characterized in that the taste-masking composition has a molar ratio neohesperidin dihydrochalcone:cyclodextrin which is comprised between 1.5:1 and 1:6.

31.—Process according to embodiment 30, characterized in that the taste-masking composition has a molar ratio neohesperidin dihydrochalcone:cyclodextrin which is comprised between 1.2:1 and 1:4.

32.—Process according to embodiment 31, characterized in that the taste-masking composition has a molar ratio neohesperidin dihydrochalcone:cyclodextrin which is comprised between 1.1:1 and 1:3.5.

33.—Process according to embodiment 32, characterized in that the taste-masking composition has a molar ratio neohesperidin dihydrochalcone:cyclodextrin which is comprised between 1:1 and 1:3.

34.—Process according to any one of embodiments 28 to 33, characterized in that the taste-masking composition has a molar ratio neohesperidin dihydrochalcone:cyclodextrin which is 1:1.

35.—Process according to any one of embodiments 28 to 33, characterized in that the taste-masking composition has a molar ratio neohesperidin dihydrochalcone:cyclodextrin which is about 1:1.

36.—Process according to any one of embodiments 28 to 33, characterized in that the taste-masking composition has a molar ratio neohesperidin dihydrochalcone:cyclodextrin which is 1±0.1:1±0.1.

37.—Process according to embodiment 36, characterized in that the taste masking composition has a molar ratio neohesperidin dihydrochalcone:cyclodextrin which is 1±0.05:1±0.05.

38.—Process according to any one of embodiments 28 to 33, characterized in that the taste-masking composition has a molar ratio neohesperidin dihydrochalcone:cyclodextrin which is 1:3.

39.—Process according to any one of embodiments 28 to 33, characterized in that the taste-masking composition has a molar ratio neohesperidin dihydrochalcone:cyclodextrin which is about 1:3.

40.—Process according to any one of embodiments 28 to 33, characterized in that the taste-masking composition has a molar ratio neohesperidin dihydrochalcone:cyclodextrin which is 1±0.1:3±0.3.

41.—Process according to embodiment 40, characterized in that the taste-masking composition has a molar ratio neohesperidin dihydrochalcone:cyclodextrin which is 1±0.05:3±0.15.

42.—Process according to any one of embodiments 28 to 41, characterized in that the unpleasant taste is bitterness and/or astringency.

43.—Process according to any one of embodiments 28 to 42, characterized in that the unpleasantly tasting substance is selected from the group consisting of: caffeine, ibuprofen, limonin, naringin, paracetamol, aspirin, potassium chloride, quercetin, quinine, theobromine, catechin, epigallocatechin gallate, epigallocatechin, epicatechin gallate, epicatechin, dextromethorphan, phenylephrine, guaifenesin, bismuth subsalicylate, soy protein, whey protein, pea protein, aspartame, sucralose, saccharin, stevia extracts and mixtures thereof.

44.—Process according to embodiment 43, characterized in that the unpleasantly tasting substance is selected from the group consisting of: caffeine, naringin, paracetamol, potassium chloride, proteins, catechins, sucralose, stevia extracts and mixtures thereof.

45.—Process according to any one of embodiments 28 to 44, characterized in that the ingestible product is selected from a food product and a pharmaceutical product.

46.—Process according to embodiment 45, characterized in that the ingestible product is a pharmaceutical product containing a bitter active ingredient selected from paracetamol, ibuprofen, aspirin, dextromethorphan, phenylephrine, guaifenesin and bismuth subsalicylate.

47.—Process according to embodiment 45, characterized in that the ingestible product is a food product which comprises a bitter or astringent substance selected from caffeine, limonin, naringin, potassium chloride, quercetin, quinine, catechins, soy protein, whey protein, pea protein, aspartame, sucralose, saccharin and stevia extracts.

48.—Ingestible product which contains at least one unpleasantly tasting substance and a taste-masking composition, wherein the taste-masking composition comprises neohesperidin dihydrochalcone and a cyclodextrin selected from beta-cyclodextrin and gamma-cyclodextrin.

49.—Ingestible product according to embodiment 48, characterized in that the unpleasantly tasting substance is a bitter or an astringent substance.

50.—Ingestible product according to embodiment 48 or 49, characterized in that the unpleasantly tasting substance is selected from the group consisting of: caffeine, ibuprofen, limonin, naringin, paracetamol, aspirin, potassium chloride, quercetin, quinine, theobromine, catechin, epigallocatechin gallate, epigallocatechin, epicatechin gallate, epicatechin, dextromethorphan, phenylephrine, guaifenesin, bismuth subsalicylate, soy protein, whey protein, pea protein, aspartame, sucralose, saccharin, stevia extracts and mixtures thereof.

51.—Ingestible product according to any one of embodiments 48 to 50, characterized in that the unpleasantly tasting substance is selected from the group consisting of: caffeine, naringin, paracetamol, potassium chloride, proteins, catechins, sucralose, stevia extracts and mixtures thereof.

52.—Ingestible product according to any one of embodiments 48 to 51, characterized in that the ingestible product is selected from a food product and a pharmaceutical product.

53.—Ingestible product according to embodiment 52, characterized in that it is a pharmaceutical product containing an unpleasantly tasting substance which is a bitter active ingredient selected from paracetamol, ibuprofen, aspirin, dextromethorphan, phenylephrine, guaifenesin and bismuth subsalicylate.

54.—Ingestible product according to embodiment 52, characterized in that it is a food product containing an unpleasantly tasting substance which is a bitter or astringent substance selected from caffeine, limonin, naringin, potassium chloride, quercetin, quinine, catechins, soy protein, whey protein, pea protein, aspartame, sucralose, saccharin and stevia extracts.

55.—Ingestible product according to any one of embodiments 48 to 54, characterized in that the taste-masking composition has a molar ratio neohesperidin dihydrochalcone:cyclodextrin which is comprised between 1.5:1 and 1:10.

56.—Ingestible product according to any one of embodiments 48 to 55, characterized in that the taste-masking composition has a molar ratio neohesperidin dihydrochalcone:cyclodextrin which is comprised between 1.5:1 and 1:16.

57.—Ingestible product according to embodiment 56, characterized in that the taste-masking composition has a molar ratio neohesperidin dihydrochalcone:cyclodextrin which is comprised between 1.2:1 and 1:4.

58.—Ingestible product according to embodiment 57, characterized in that the taste-masking composition has a molar ratio neohesperidin dihydrochalcone:cyclodextrin which is comprised between 1.1:1 and 1:3.5.

59.—Ingestible product according to embodiment 58, characterized in that the taste-masking composition has a molar ratio neohesperidin dihydrochalcone:cyclodextrin which is comprised between 1:1 and 1:3.

60.—Ingestible product according to any one of embodiments 48 to 59, characterized in that the taste-masking composition has a molar ratio neohesperidin dihydrochalcone:cyclodextrin which is 1:1.

61.—Ingestible product according to any one of embodiments 48 to 59, characterized in that the taste-masking composition has a molar ratio neohesperidin dihydrochalcone:cyclodextrin which is about 1:1.

62.—Ingestible product according to any one of embodiments 48 to 59, characterized in that the taste-masking composition has a molar ratio neohesperidin dihydrochalcone:cyclodextrin which is 1±0.1:1±0.1.

63.—Ingestible product according to embodiment 62, characterized in that the taste-masking composition has a molar ratio neohesperidin dihydrochalcone:cyclodextrin which is 1±0.05:1±0.05.

64.—Ingestible product according to any one of embodiments 48 to 59, characterized in that the taste-masking composition has a molar ratio neohesperidin dihydrochalcone:cyclodextrin which is 1:3.

65.—Ingestible product according to any one of embodiments 48 to 59, characterized in that the taste-masking composition has a molar ratio neohesperidin dihydrochalcone:cyclodextrin which is about 1:3.

66.—Ingestible product according to any one of embodiments 48 to 59, characterized in that the taste-masking composition has a molar ratio neohesperidin dihydrochalcone:cyclodextrin which is 1±0.1:3±0.3.

67.—Ingestible product according to embodiment 66, characterized in that the taste-masking composition has a molar ratio neohesperidin dihydrochalcone:cyclodextrin which is 1±0.05:3±0.15.

68.—Ingestible product according to any one of embodiments 48 to 67, characterized in that the cyclodextrin is beta-cyclodextrin.

69.—Ingestible product according to any one of embodiments 48 to 67, characterized in that the cyclodextrin is gamma-cyclodextrin.

70.—Taste-masking composition comprising neohesperidin dihydrochalcone and gamma-cyclodextrin.

71.—Taste-masking composition according to embodiment 70, characterized in that it is a mixture of neohesperidin dihydrochalcone and gamma-cyclodextrin.

72.—Taste-masking composition according to embodiment 70, characterized in that neohesperidin dihydrochalcone and gamma-cyclodextrin are in the form of a complex.

73.—Taste masking composition according to any one of embodiments 70 to 72, characterized in that the molar ratio neohesperidin dihydrochalcone:gamma-cyclodextrin is comprised between 1.5:1 and 1:10.

74.—Taste masking composition according to any one of embodiments 70 to 73, characterized in that the molar ratio neohesperidin dihydrochalcone:gamma-cyclodextrin is comprised between 1.5:1 and 1:6.

75.—Taste masking composition according to embodiment 74, characterized in that the molar ratio neohesperidin dihydrochalcone:gamma-cyclodextrin is comprised between 1.2:1 and 1:4.

76.—Taste masking composition according to embodiment 75, characterized in that the molar ratio neohesperidin dihydrochalcone:gamma-cyclodextrin is comprised between 1.1:1 and 1:3.5.

77.—Taste masking composition according to any one of embodiments 70 to 76, characterized in that the molar ratio neohesperidin dihydrochalcone:gamma-cyclodextrin is comprised between 1:1 and 1:3.

78.—Taste masking composition according to any one of embodiments 70 to 77, characterized in that the molar ratio neohesperidin dihydrochalcone:gamma-cyclodextrin is 1:1.

79.—Taste masking composition according to any one of embodiments 70 to 77, characterized in that the molar ratio neohesperidin dihydrochalcone:gamma-cyclodextrin is about 1:1.

80.—Taste masking composition according to any one of embodiments 70 to 77, characterized in that the molar ratio neohesperidin dihydrochalcone:gamma-cyclodextrin is 1±0.1:3±0.3.

81.—Taste masking composition according to embodiment 80, characterized in that the molar ratio neohesperidin dihydrochalcone:gamma-cyclodextrin is 1±0.05:3±0.15.

82.—Taste masking composition according to any one of embodiments 70 to 77, characterized in that the molar ratio neohesperidin dihydrochalcone:gamma-cyclodextrin is 1:3.

83.—Taste masking composition according to any one of embodiments 70 to 77, characterized in that the molar ratio neohesperidin dihydrochalcone:gamma-cyclodextrin is about 1:3.

84.—Taste masking composition according to any one of embodiments 70 to 77, characterized in that the molar ratio neohesperidin dihydrochalcone:gamma-cyclodextrin is 1±0.1:3±0.3.

85.—Taste masking composition according to embodiment 84, characterized in that the molar ratio neohesperidin dihydrochalcone:gamma-cyclodextrin is 1±0.05:3±0.15.

The following examples further illustrate the invention.

EXAMPLES

Example 1: Sweetening Compositions

Several sweetening compositions according to the present invention were prepared, using different molar ratios between neohesperidin dihydrochalcone (NHDC) and gamma-cyclodextrin (gCD), as disclosed in Table 1. NHDC was supplied by Ferrer HealthTech and gamma-cyclodextrin was supplied by Wacker.

From the molar masses of NHDC (613) and gamma-cyclodextrin (1297), the weight percentage of NHDC contained in each composition was calculated.

TABLE 1

| Sweetening agent | NHDC:gCD ratio | NHDC weight % |
| --- | --- | --- |
| Example A | 1:1 | 32.10 |
| Example B | 1:3 | 13.61 |
| Example C | 1.5:1 | 41.48 |
| Example D | 1:6 | 7.30 |
| Example E | 1:10 | 4.51 |

Sweetening compositions employed were in the form of a complex.

For preparing the complex of Example A, NHDC (14.0 g, 20.6 mmol) was added to a stirred solution of gCD (30 g, 20.6 mmol) in deionized water (500 ml). The mixture was stirred for one hour at 20-25° C., until complete dissolution. The solution was clarified through a 0.8 μm filter to remove insoluble particles. The solvent was removed under reduced pressure. A whitish solid (40 g) of 1:1 complex was obtained.

For preparing the complex of Example B, NHDC (7.5 g, 11 mmol) was added to a stirred solution of gCD (47.7 g, 33 mmol) in deionized water (500 ml). The mixture was stirred for one hour at 20-25° C., until complete dissolution. The solution was clarified through a 0.8 μm filter to remove insoluble particles. The solvent was removed under reduced pressure. A whitish solid (54 g) of 1:3 complex was obtained.

Complexes of Examples C-E were prepared under the same conditions as those above described for Examples A and B.

Example 2: Comparative Sweetening Compositions

For comparative purposes, equivalent sweetening compositions to Examples A and B were prepared, but using beta-cyclodextrin, instead of gamma-cyclodextrin, also in the form of a complex. Thus, Comparative Examples A and B were prepared, using the molar ratios between NHDC and beta-cyclodextrin (bCD) disclosed in Table 2. Beta-cyclodextrin was supplied by Wacker.

Analogously to Example 1, using the molar masses of NHDC (613) and beta-cyclodextrin (1138), the weight percentage of NHDC contained in each composition was calculated.

TABLE 2

| Sweetening agent | NHDC:bCD ratio | NHDC weight % |
| --- | --- | --- |
| Comparative Example A | 1:1 | 35.07 |
| Comparative Example B | 1:3 | 15.26 |

For preparing the complex of Comparative Example A, NHDC (7.0 g, 10.2 mmol) was added to a stirred solution of bCD (13.4 g, 10.2 mmol) in deionized water (900 ml) at 50° C. The mixture was stirred for two hours at 50° C., until complete dissolution. The solution was clarified through a 0.8 μm filter to remove insoluble particles. The solvent was removed under reduced pressure. A whitish solid (18.1 g) of 1:1 complex was obtained.

For preparing the complex of Comparative Example B, NHDC (4.0 g, 5.8 mmol) was added to a stirred solution of bCD (22.9 g, 17.5 mmol) in deionized water (1500 ml) at 50° C. The mixture was stirred for two hours at 50° C., until complete dissolution. The solution was clarified through a 0.8 μm filter to remove insoluble particles. The solvent was removed under reduced pressure. A whitish solid (23.9 g) of 1:3 complex was obtained.

Example 3: Sweetening Synergy Tests

A sensory test was performed to assess the sweetening synergism achieved with the composition of the invention (Examples A and B), and this effect was also compared to the effect obtained with analogous compositions containing beta-cyclodextrin (Comparative Examples A and B). Further compositions of the present invention (Examples C, D and E) were also assessed in this sensory test.

A group of expert panellists in sweet descriptors evaluated the sweetness of the different compositions as well as that of the ingredients NHDC, beta-cyclodextrin and gamma-cyclodextrin used alone.

Each evaluated sweetening agent was dissolved in water at different concentrations, at room temperature. The panel then determined, for each product, the concentration that was equisweet to the reference solutions of 1% and 3% sucrose in water. The results are summarized in Table 3 (Examples A and B are abbreviated as Ex. A and Ex. B, respectively, and the Comparative Examples A and B are abbreviated as Comp. A and Comp. B, respectively).

TABLE 3

| | NHDC | Ex. A NHDC:gCD 1:1 | Ex. B NHDC:gCD 1:3 | Ex. C NHDC:gCD 1.5:1 | Ex. D NHDC:gCD 1:6 | Ex. E NHDC:gCD 1:10 | Comp. A NHDC:bCD 1:1 | Comp. B NHDC:bCD 1:3 |
|---|---|---|---|---|---|---|---|---|
| | | | | Sweetening agent | | | | |
| | | | | 1% sucrose (real sweetness) | | | | |
| Equisweet concentration (ppm) | 5.0 | 12.0 | 26.0 | 9.0 | 50.0 | 85.0 | 17.0 | 50.0 |
| NHDC amount (ppm) | (5.0) | (3.9) | (3.5) | (3.6) | (3.9) | (3.7) | (6.1) | (7.7) |
| | | | | 3% sucrose (real sweetness) | | | | |
| Equisweet concentration (ppm) | 24.0 | 42.0 | 90.0 | 32.0 | 180.0 | 300.0 | 82.0 | 185.0 |
| NHDC amount (ppm) | (24.0) | (13.5) | (12.2) | (12.7) | (13.0) | (13.0) | (28.8) | (28.3) |

Since beta- and gamma-cyclodextrins are also sweet compounds, the equisweet concentrations of both cyclodextrins were also determined by the test panel to assess their possible contribution to the sweetness of the composition. It was found that the concentration of beta-cyclodextrin equisweet to 1% and 3% sucrose was 12000 and 70000 ppm, respectively, and the equivalent equisweet concentrations for gamma-cyclodextrin were 25000 and 85000 ppm. Therefore, as the equisweet concentrations of both cyclodextrins are at least three orders of magnitude larger than those of NHDC, it was concluded that their contribution to the sweetness was negligible.

The first row of data for each sucrose level in Table 3 shows the equisweet concentrations (in ppm) for each evaluated agent, whereas in the second row, the amount of pure NHDC (in ppm) which is present in those equisweet concentrations is calculated. These results are graphically shown in FIGS. 1 and 2.

A more quantitative evaluation of the sweetness synergy provided by the compositions of the present invention was performed by comparing the real measured sweetness of the compositions comprising gamma-cyclodextrin and NHDC with the theoretical sweetness expected from the sum of the individual contribution of each component in the composition.

To this end, the relative sweetening power of each component was first calculated. For comparative purposes, the relative sweetening power of beta-cyclodextrin was also calculated. The relative sweetening power of a given compound, at a given sweetness level, indicates how many times sweeter this compound is than sucrose. It is therefore calculated as the ratio between the concentration of sucrose and the equisweet concentration of each ingredient, for each sweetness level. The relative sweetening powers of NHDC, beta-cyclodextrin (bCD) and gamma-cyclodextrin (gCD) are shown in Table 4.

TABLE 4

| | Individual ingredient | | |
|---|---|---|---|
| | NHDC | bCD | gCD |
| | 1% sucrose (real sweetness) | | |
| Equisweet concentration (ppm) | 5 | 12000 | 25000 |
| Relative sweetening power | 2000 | 0.8333 | 0.4000 |
| | 3% sucrose (real sweetness) | | |
| Equisweet concentration (ppm) | 24 | 70000 | 85000 |
| Relative sweetening power | 1250 | 0.4286 | 0.3529 |

From the relative sweetening power of each ingredient, it is possible to calculate the expected sweetness (sucrose equivalence) of a blend of those ingredients, according to Formula I:

Expected sweetness (sucrose equivalence) of a blend $C1+C2$=Concentration of compound $C1 \times$relative sweetening power of compound $C1$+Concentration of compound $C2 \times$relative sweetening power of compound $C2$ Then, the sweetness synergy of a blend of components can be calculated according to Formula II:

$$\text{Sweetness synergy} = \frac{\text{Real sweetness} - \text{Expected sweetness}}{\text{Expected sweetness}}$$

Tables 5 and 6 below show the expected (theoretical) sweetness and the sweetness synergy for the compositions of the present invention (Examples A and B) and, for comparative purposes, also for the Comparative Examples A and B, containing the combination of NHDC and beta-cyclodextrin, for 1% sucrose level (Table 5) and 3% sucrose level (Table 6).

TABLE 5

| 1% sucrose (real sweetness) | Ex. A NHDC:gCD 1:1 | Ex. B NHDC:gCD 1:3 | Comp. A NHDC:bCD 1:1 | Comp. B NHDC:bCD 1:3 | Ex. C NHDC:gCD 1.5:1 | Ex. D NHDC:gCD 1:6 | Ex. E NHDC:gCD 1:10 |
|---|---|---|---|---|---|---|---|
| Equisweet conc. (ppm) | 12.00 | 26.00 | 17.50 | 50.00 | 9.00 | 50.00 | 85.00 |
| NHDC contained (ppm) | 3.85 | 3.54 | 6.14 | 7.65 | 3.56 | 3.62 | 3.69 |
| gCD/bCD contained (ppm) | 8.12 | 22.46 | 11.36 | 42.35 | 5.44 | 46.38 | 81.31 |
| Expected sweetness (%) | 0.77 | 0.72 | 1.24 | 1.57 | 0.81 | 0.82 | 0.84 |
| Sweetness synergy (%) | 29.9 | 38.9 | -19.4 | -36.3 | 23.4 | 21.2 | 18.6 |

TABLE 6

|  | Ex. A NHDC:gCD | Ex. B NHDC:gCD | Comp. A NHDC:bCD | Comp. B NHPD:bCD | Ex. C NHDC:gCD | Ex. D NHDC:gCD | Ex. E NHDC:gCD |
|---|---|---|---|---|---|---|---|
| 3% sucrose (real sweetness) | 1:1 | 1:3 | 1:1 | 1:3 | 1.5:1 | 1:6 | 1:10 |
| Equisweet conc. (ppm) | 42.00 | 90.00 | 82.00 | 185.00 | 32.00 | 180.00 | 300.00 |
| NHDC contained (ppm) | 13.48 | 12.24 | 28.78 | 28.31 | 12.67 | 13.02 | 13.03 |
| gCD/bCD contained (ppm) | 28.52 | 77.76 | 53.22 | 156.69 | 17.64 | 158.34 | 264.17 |
| Expected sweetness (%) | 1.70 | 1.56 | 3.62 | 3.61 | 1.80 | 1.86 | 1.86 |
| Sweetness synergy (%) | 76.5 | 92.3 | −17.1 | −16.9 | 66.6 | 61.5 | 61.1 |

For example, for 1% sucrose level (Table 5), the expected sweetness of 12 ppm of the composition of Example A (first column) is calculated using Formula I, as follows: 3.85 $10^{-4} \times 2000 + 8.12 \ 10^{-4} \times 0.4$, i.e., 0.77% sucrose equivalence. Since the real sweetness is equivalent to 1% sucrose, the synergy can be calculated using Formula II, as follows: 1−0.77/0.77, i.e., 29.9% synergy.

Analogously, for 3% sucrose level (Table 6), the expected sweetness of 42 ppm of the composition of Example A (first column) is calculated using Formula I, as follows: 13.48 $10^{-4} \times 1250 + 28.52 \ 10^{-4} \times 0.3529$, i.e., 1.70% sucrose equivalence. Then, the synergy can be calculated using Formula II, as follows: (3−1.70)/1.70, i.e., 76.5% synergy.

All the values of expected sweetness and sweetness synergy in Tables 5 and 6 were calculated analogously, using the appropriate values of the relative sweetening power (according to Table 4) and the appropriate real sweetness value (either 1% or 3%).

Example 4: Evolution of the Sweetening Power with the Sweetness Level

As disclosed above in Example 3, the relative sweetening power of a given compound, at a given sweetness level, indicates how many times sweeter than sucrose the compound is, and the value is calculated as the ratio between the concentration of sucrose and the equisweet concentration of the compound.

The relative sweetening power of NHDC at 1% and 3% sucrose levels was calculated in Example 3, and is shown in Table 4.

The sweetening power of the compositions of the invention relative to sucrose can analogously be calculated, at a given sucrose level. Thus, for example, since 12 and 42 ppm of the composition of Example A are equisweet to 1% and 3% sucrose solutions, respectively (see Table 3), it follows that the composition of Example A is 833 and 714 times sweeter than sucrose, at 1% and 3% sucrose levels, respectively.

Similarly, since 26 and 90 ppm of the composition of Example B are equisweet to 1% and 3% sucrose solutions, respectively (see Table 3), it follows that the composition of Example B is 385 and 333 times sweeter than sucrose, at 1% and 3% sucrose levels, respectively.

The values of the relative sweetening power of each substance, and also those of compositions of Examples A-D are summarized below in Table 7.

TABLE 7

|  |  | Relative sweetening power | | | |
|---|---|---|---|---|---|
| Sucrose level | NHDC | Ex. A NHDC:gCD 1:1 | Ex. B NHDC:gCD 1:3 | Ex. C NHDC:gCD 1.5:1 | Ex. D NHDC:gCD 1:6 |
| 1% | 2000 | 833 | 385 | 1111 | 200 |
| 3% | 1250 | 714 | 333 | 937 | 167 |

Figure 3:
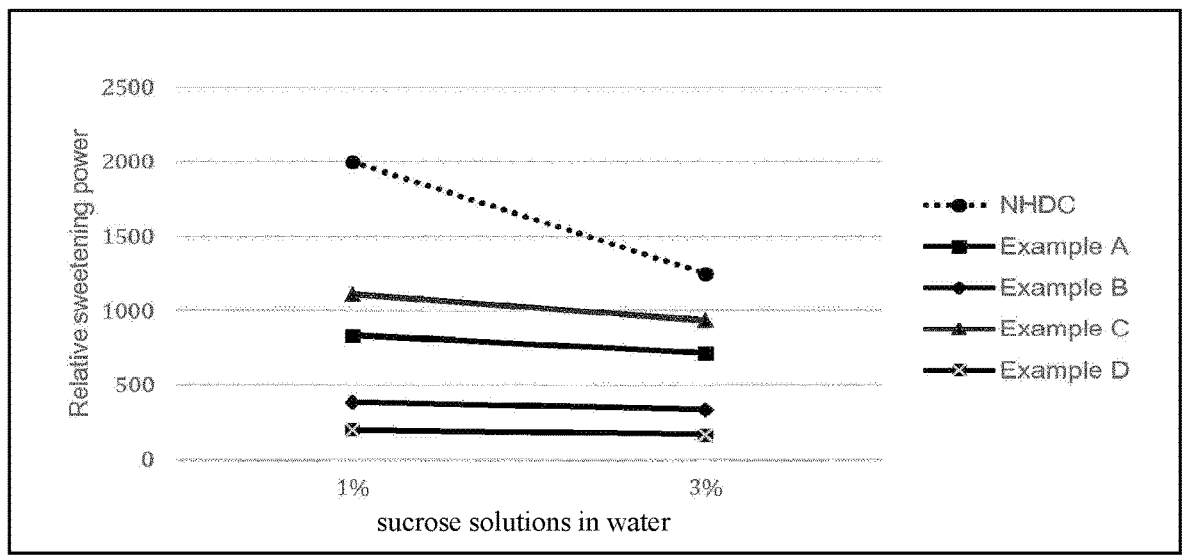
FIG. 3 represents the sweetening power relative to sucrose of the tested compositions, at different sweetness levels. The ordinate represents the relative sweetening power and the abscissa represents the sweetness levels, namely, equivalent to 1% and 3% sucrose solutions. The tested substances were neohesperidin dihydrochalcone alone (NHDC, black circles), and in combination with gamma-cyclodextrin in a molar ratio NHDC:gamma-cyclodextrin 1:1 (Example A, squares), 1:3 (Example B, diamonds), 1.5:1 (Example C, triangles) and 1:6 (Example D, crosses).

The results of Table 7 are represented in the graphic of FIG. 3.

Example 5: Taste Profile

The overall taste profile achieved with the sweetening composition of the present invention was evaluated and compared with the target taste profile of sucrose.

For this assay, all samples were evaluated at the same sweetness level, so each sample was used at a concentration which was equisweet to 3% sucrose. For each sample, the following parameters were evaluated:

Time to first sweetness detection

Time to maximum sweetness

Lingering (time for the sweetness to disappear)

Off-flavour: menthol, liquorice (any tastes that are different from sweetness)

Mouthfeel (density, i.e., the perceived viscosity in the mouth)

These evaluations were carried out by a calibrated taste panel, and conducted at room temperature.

Each of those parameters was evaluated on a 0- to 5-point scale. The values for sucrose were the reference, and were considered the target to emulate.

The results obtained with this test are summarized in the following table:

TABLE 8

| Sensory descriptors | Sucrose (3%) | NHDC (24 ppm) | Ex. A (42 ppm) | Ex. B (90 ppm) |
|---|---|---|---|---|
| Total sweetness | 5.00 | 5.00 | 5.00 | 5.00 |
| Time to first sweetness | 1.00 | 3.75 | 3.25 | 3.00 |
| Time to maximum sweetness | 2.00 | 4.25 | 3.25 | 2.75 |
| Lingering | 2.00 | 4.00 | 3.50 | 2.75 |
| Off-flavour: menthol, licorice | 0.00 | 3.25 | 2.50 | 2.00 |
| Mouthfeel (density) | 4.00 | 1.75 | 2.50 | 3.00 |

The results of Table 8 are shown graphically in FIG. 4, in the form of a spider graph.

Example 6: Sweetened Beverage

A reference orange soft drink sweetened with high fructose corn syrup (HFCS) was prepared, using the ingredients listed in Table 9 (Formula 1). All the percentages in the table are by weight.

TABLE 9

| Ingredient | Formula 1 (Reference) | Formula 2 | Formula 3 |
|---|---|---|---|
| HFCS-42* (71 °Bx) | 15.27% | 13.75% | 13.75% |
| (sugar reduction) | (0%) | (10%) | (10%) |
| NHDC | — | 10 ppm | — |
| Example B (NHDC:bCD 1:3) (NHDC-content) | — | — | 33 ppm (4.5 ppm) |
| Sodium benzoate | 0.02% | 0.02% | 0.02% |
| Potassium sorbate | 0.02% | 0.02% | 0.02% |
| Citric acid | 0.34% | 0.34% | 0.34% |
| Orange soda colour | 0.05% | 0.05% | 0.05% |
| Orange soda flavour | 0.22% | 0.22% | 0.22% |
| Water | 84.08% | 85.61% | 85.61% |
| Total | 100.00% | 100.00% | 100.00% |

*HFCS-42 = HFCS with 42% fructose content.

For preparing the beverages, the following process was followed. The high fructose corn syrup was weighed in a 1 L beaker. The remaining minor ingredients (sodium benzoate, potassium sorbate, citric acid, orange soda colour and orange soda flavour) were separately weighed in small beakers, and water was added to each of the small beakers and mixed until solubilizing each ingredient. Once dissolved, all those minor ingredients were added to the 1 L beaker with the HFCS. The obtained solution was thoroughly mixed and water was added gradually to 1 Kg.

For assaying the possible substitution of HFCS with NHDC and with the composition of the present invention (Example B), a 0.1% mother solution of NHDC in water was prepared by gradually adding 0.1 g of NHDC to 99.9 g of water, mixing, and heating to 66° C. during 15 minutes until a yellowish solution was obtained; the solution was then left to cool to room temperature. Analogously, a 1% mother solution of Example B in water was prepared by adding 1 g of Example B to 99 g of water and mixing, thus obtaining a yellowish solution.

Maximum sugar substitution with NHDC was then determined by replacing increasing amounts of HFCS by NHDC and then passing the reference and the prototype through a triangular test by a calibrated panel. Hence, the criterion to determine the maximum sugar substitution was not merely the equisweetness between the reference and the prototype but the overall taste profile.

Maximum sugar substitution reached with NHDC without any noticeable difference in a triangular test was 10% (Formula 2 of Table 9). This substitution was obtained with 10 ppm of NHDC.

In a second step, the panel determined the amount of Example B (composition containing a molar ratio NHDC:bCD of 1:3) to obtain the same sugar substitution. The same 10% sugar substitution was reached with 33 ppm of the composition of Example B, which contained 4.5 ppm of NHDC (Formula 3 of Table 9).

Example 7: Sweetened Beverage

The purpose of this example was to maximize the sugar substitution in an orange juice based soft drink while maintaining the same overall taste profile. A calibrated panel was not able to distinguish the reference from the different prototypes in triangular testing.

The reference product (Formula 1 of Table 10) contained 10% added sucrose. The maximum sucrose substitution achieved with NHDC was 15% out of the initial 10%, by using 10 ppm of NHDC (Formula 2 of Table 10). With the sweetening composition of the present invention, it was possible to increase the sucrose substitution, up to 25% without changing the taste profile of the beverage (Formula 3 of Table 10).

The composition of each beverage is disclosed in Table 10. For the preparation of these beverages, an orange juice concentrate 65° Bx (Dallant) and orange flavor #2N341/C (Dallant) were used. All the percentages in the table are by weight.

TABLE 10

| Ingredient | Formula 1 (Reference) | Formula 2 | Formula 3 |
|---|---|---|---|
| Sucrose | 10.000% | 8.500% | 7.500% |
| (sucrose reduction) | (0%) | (15%) | (25%) |
| NHDC | — | 8.0 ppm | — |
| Example B (NHDC:bCD 1:3) (NHDC-content) | — | — | 80.0 ppm (10.9 ppm) |
| Orange juice concentrate (65 °Bx) | 1.850% | 1.850% | 1.850% |
| Sodium Benzoate | 0.015% | 0.015% | 0.015% |
| Citric Acid | 0.225% | 0.225% | 0.225% |
| Orange flavour | 0.100% | 0.100% | 0.100% |
| Orange Colour | 0.100% | 0.100% | 0.100% |
| Water | 87.710% | 89.210% | 90.210% |
| Total | 100.00% | 100.00% | 100.00% |

Example 8: Sweetened Dark Chocolate

Different formulas of sweetened dark chocolate were prepared using the ingredients listed in Table 11. The percentages in the table are expressed by weight.

TABLE 11

| Ingredient | Formula 1 (Reference) | Formula 2 | Formula 3 | Formula 4 |
|---|---|---|---|---|
| Powdered sugar | 6.00% | 5.40% | 4.91% | 4.32% |
| (sugar reduction) | | (10.00%) | (18.17%) | (28.00%) |
| 1% NHDC glycerol sol. (NHDC-content) | — | 0.03% (3 ppm) | — | — |
| Example B composition (NHDC:bCD 1:3) (NHDC-content) | — | — | 0.0022% (3 ppm) | 0.004% (5.45 ppm) |
| Chocolate 70% cacao | until 100% | until 100% | until 100% | until 100% |
| Total | 100.00% | 100.00% | 100.00% | 100.00% |

The reference product (Formula 1 of Table 11) contained a commercial chocolate with 70% cacao content (Lindt®) and 6% of powdered sugar.

Along all the assays performed, the goal was to maximize the sucrose substitution while maintaining the same overall taste profile. A calibrated panel was not able to distinguish the reference from the different prototypes tested.

In a first test, maximum sucrose substitution with NHDC alone was assessed. In this case, NHDC was added in the form of a 1% solution in glycerol, and the maximum sugar substitution in this case was 10% of sucrose (out of the initial 6% of the formula). This reduction was achieved using 0.03% of the glycerol solution, equivalent to 3 ppm of NHDC (Formula 2 of Table 11).

Using the same amount of pure NHDC, i.e., 3 ppm, but contained within the composition of Example B (equivalent to 22 ppm of Example B), it was found that it was possible to substitute a larger percentage of sugar of the reference product, up to 18.17% of sugar (Formula 3 of Table 11).

In a further assay, the maximum sucrose substitution with the composition of Example B was determined. Using this composition, it was possible to reduce up to the 28% of sugar of the reference product, without changing the taste profile of the product, using 40 ppm of Example B (containing 5.45 ppm of NHDC) (Formula 4 of Table 11).

The method used for preparing the dark chocolate products of this assay was as follows. Firstly, 1% solution of NHDC in glycerol was prepared by gradually adding 1 g of NHDC to 99 g of glycerol, mixing and heating to 60° C. for 15 minutes, until a transparent solution is obtained. The solution was left to cool off to room temperature. The dark chocolate was weighed and heated to 45° C. and, when the chocolate was completely melted, powdered sugar was added and, optionally, also the 1% NHDC glycerol solution or the composition of Example B, and the mixture was then thoroughly mixed. The mixture was heated until reaching 45° C., then it was let to cool to 30° C., and then it was poured into molds (6 g/piece). The molds with the chocolate were put in the fridge for a quicker hardening.

Example 9: Taste-Masking Compositions

Different taste-masking compositions were prepared, as complexes of neohesperidin dihydrochalcone with gamma-cyclodextrin (gCD) or beta-cyclodextrin (bCD), using different molar ratios, as disclosed in Table 12. NHDC was supplied by the company Ferrer HealthTech and cyclodextrins were supplied by Wacker

TABLE 12

| Taste-masking agent | cyclodextrin | NHDC:CD ratio |
| --- | --- | --- |
| Example A | gCD | 1:1 |
| Example B | gCD | 1:3 |
| Example C | gCD | 1.5:1 |
| Example D | gCD | 1:6 |
| Example E | gCD | 1:10 |
| Example F | bCD | 1:1 |
| Example G | bCD | 1:3 |

The sweetening compositions employed were in the form of a complex.

For preparing the complex of Example A, NHDC (14.0 g, 20.6 mmol) was added to a stirred solution of gCD (30 g, 20.6 mmol) in deionized water (500 ml). The mixture was stirred for one hour at 20-25° C., until complete dissolution. The solution was clarified through a 0.8 µm filter to remove insoluble particles. The solvent was removed under reduced pressure. A whitish solid (40 g) of 1:1 complex was obtained.

For preparing the complex of Example B, NHDC (7.5 g, 11 mmol) was added to a stirred solution of gCD (47.7 g, 33 mmol) in deionized water (500 ml). The mixture was stirred for one hour at 20-25° C., until complete dissolution. The solution was clarified through a 0.8 µm filter to remove insoluble particles. The solvent was removed under reduced pressure. A whitish solid (54 g) of 1:3 complex was obtained.

NHDC-gCD complexes of Examples C, D and E were prepared under the same conditions as those above described for Examples A and B.

For preparing the complex of Example F, NHDC (7.0 g, 10.2 mmol) was added to a stirred solution of bCD (13.4 g, 10.2 mmol) in deionized water (900 ml) at 50° C. The mixture was stirred for two hours at 50° C., until complete dissolution. The solution was clarified through a 0.8 µm filter to remove insoluble particles. The solvent was removed under reduced pressure. A whitish solid (18.1 g) of 1:1 complex was obtained.

For preparing the complex of Example G, NHDC (4.0 g, 5.8 mmol) was added to a stirred solution of bCD (22.9 g, 17.5 mmol) in deionized water (1500 ml) at 50° C. The mixture was stirred for two hours at 50° C., until complete dissolution. The solution was clarified through a 0.8 µm filter to remove insoluble particles. The solvent was removed under reduced pressure. A whitish solid (23.9 g) of 1:3 complex was obtained.

Example 10: Masking Bitterness of Paracetamol

The bitter masking effect against paracetamol was assayed. The antibittering effect was measured as a dose-response profile vs. a solution of paracetamol.

The following substances were assayed: NHDC alone, gamma-cyclodextrin alone and compositions comprising NHDC and gamma-cyclodextrin in a molar ratio 1:3 (Example B), 1.5:1 (Example C), 1:6 (Example D) and 1:10 (Example E).

For evaluating the masking effect of each substance, several aqueous solutions were prepared, each containing 5000 ppm of paracetamol and different concentrations of the tested substance, namely, 5, 25, 50, 75 and 100 ppm.

A calibrated test panel compared each solution with several solutions of paracetamol in water at different concentrations, and determined the equibitter paracetamol solution. The equibitter solution was calculated as the average of all the evaluations of the panel.

The masking effect was then calculated from the reference amount of paracetamol contained in each tested solution (5000 ppm) and the amount of paracetamol in the equibitter solution, using the following formula (Formula III):

$$\text{Masking effect} = \frac{5000 - \text{Equibitter amount of paracetamol}(ppm)}{5000}$$

Thus, for example, a solution containing 5000 ppm of paracetamol and 100 ppm of NHDC was equibitter to a solution containing 3266.7 ppm of paracetamol. Therefore, the masking effect was 34.67%.

In the same way, the masking effect for each substance at each concentration was calculated. The results are listed in Table 13.

TABLE 13

| | | | Masking effect (%) | | | | |
|---|---|---|---|---|---|---|---|
| Conc (ppm) | NHDC | gCD | Ex. A NHDC:gCD (1:1) | Ex. B NHDC:gCD (1:3) | Ex. C NHDC:gCD (1.5:1) | Ex. D NHDC:gCD (1:6) | Ex. E NHDC:gCD (1:10) |
| 5 | 6.00 | 1.00 | 1.33 | 2.00 | 3.00 | 6.00 | 4.00 |
| 25 | 14.00 | 2.00 | 5.67 | 6.67 | 9.00 | 7.70 | 5.30 |
| 50 | 15.33 | 4.00 | 9.33 | 12.00 | 10.00 | 9.30 | 8.70 |
| 75 | 27.00 | 5.00 | 22.00 | 18.33 | 14.00 | 12.00 | 10.70 |
| 100 | 34.67 | 6.00 | 30.67 | 27.00 | 14.50 | 15.30 | 12.00 |

For calculating the masking synergies between gamma-cyclodextrin and NHDC, first, for each amount of the combination (Examples A-E), using the molecular weight of each component, the amounts of gamma-cyclodextrin and NHDC contained therein were calculated. For example, 100 ppm of Example B contain 13.61 ppm of NHDC and 86.39 ppm of gamma-cyclodextrin. Then, the antibittering contribution of each component in the composition was calculated, on the basis of the data of Table 13. For example, 13.61 ppm of NHDC provide 9.44% masking effect and 86.39 ppm of gamma-cyclodextrin provide 5.46% masking effect (the antibittering effects for each specific concentration was calculated by interpolation of the data points in Table 13). Therefore, the expected masking effect is calculated as the sum of the contributions of each component. For example, the expected masking effect of 100 ppm of Example B is 14.90% (i.e., 9.44 plus 5.46).

Finally, the masking synergy is calculated using Formula IV:

$$\text{Masking synergy}(\%) = \frac{\text{Real masking effect} - \text{Expected masking effect}}{\text{Expected masking effect}} \times 100$$

Results corresponding to NHDC-gCD composition with 1:3 molar ratio are disclosed in Table 14.

TABLE 14

| [Ex. B] (ppm) | [gCD] (ppm) | Expected gCD masking contribution (%) | [NHDC] (ppm) | Expected NHDC masking contribution (%) | Expected masking effect (%) | Real masking effect (%) | Synergy (%) |
|---|---|---|---|---|---|---|---|
| 5 | 4.32 | 0.86 | 0.68 | 0.82 | 1.68 | 2.00 | 19.01 |
| 25 | 21.60 | 1.83 | 3.40 | 4.08 | 5.91 | 6.67 | 12.75 |
| 50 | 43.19 | 3.46 | 6.81 | 6.72 | 10.18 | 12.00 | 17.91 |
| 75 | 64.79 | 4.59 | 10.21 | 8.08 | 12.67 | 18.33 | 44.64 |
| 100 | 86.39 | 5.46 | 13.61 | 9.44 | 14.90 | 27.00 | 81.21 |

The masking effect of Examples C (NHDC:gCD 1.5:1), D (NHDC:gCD 1:6) and E (NHDC:gCD 1:10) was also evaluated. Aqueous solutions were prepared, each one of them containing 5000 ppm of paracetamol and different concentrations of each one of the tested formulations Ex. C-E, namely, 25 and 50 ppm. Results are disclosed in Tables 15 to 17.

TABLE 15

| [Ex. C] (ppm) | [gCD] (ppm) | Expected gCD masking contribution (%) | [NHDC] (ppm) | Expected NHDC masking contribution (%) | Expected masking effect (%) | Real masking effect (%) | Synergy (%) |
|---|---|---|---|---|---|---|---|
| 25 | 14.55 | 1.16 | 10.45 | 5.85 | 7.02 | 9.00 | 28.28 |
| 50 | 29.10 | 2.33 | 20.90 | 6.41 | 8.74 | 10.00 | 14.45 |

TABLE 16

| [Ex. D] (ppm) | [gCD] (ppm) | Expected gCD masking contribution (%) | [NHDC] (ppm) | Expected NHDC masking contribution (%) | Expected masking effect (%) | Real masking effect (%) | Synergy (%) |
|---|---|---|---|---|---|---|---|
| 25 | 23.10 | 1.85 | 1.90 | 1.06 | 2.91 | 7.67 | 163.28 |
| 50 | 46.20 | 3.70 | 3.80 | 1.17 | 4.86 | 9.33 | 91.99 |

TABLE 17

| [Ex. E] (ppm) | [gCD] (ppm) | Expected gCD masking contribution (%) | [NHDC] (ppm) | Expected NHDC masking contribution (%) | Expected masking effect (%) | Real masking effect (%) | Synergy (%) |
|---|---|---|---|---|---|---|---|
| 25 | 23.83 | 1.91 | 1.18 | 0.66 | 2.56 | 5.33 | 108.01 |
| 50 | 47.65 | 3.81 | 2.35 | 0.72 | 4.53 | 8.67 | 91.20 |

Example 11: Masking Bitterness of Quinine

The bitter masking effect against quinine was assayed, following an analogous procedure to the one used in Example 10 for paracetamol.

The following substances were assayed: NHDC alone, beta-cyclodextrin alone, a composition comprising NHDC and beta-cyclodextrin in a molar ratio 1:1 (Example F) and a composition comprising NHDC and beta-cyclodextrin in a molar ratio 1:3 (Example G).

Analogously to Example 10, several aqueous solutions were prepared, each containing 250 ppm of quinine and different concentrations of the tested substance, namely, 5, 25, 50, 75 and 100 ppm. For each tested solution, a test panel determined the equibitter quinine solution, and the masking effect was calculated using a formula analogous to formula III (substituting 5000 with 259). The masking effects for each substance at each tested concentration are listed in Table 18.

TABLE 18

| Concentration (ppm) | Masking effect (%) | | | |
|---|---|---|---|---|
| | NHDC | bCD | Example F (1:1 NHDC:bCD) | Example G (1:3 NHDC:bCD) |
| 5 | 5.00 | 0.00 | 5.00 | 1.67 |
| 25 | 13.33 | 6.67 | 20.00 | 15.00 |
| 50 | 30.00 | 11.67 | 30.00 | 31.67 |
| 75 | 48.33 | 16.67 | 33.33 | 40.00 |
| 100 | 50.00 | 13.33 | 45.00 | 48.33 |

The masking synergies between beta-cyclodextrin and NHDC in Examples F and G were calculated following an analogous procedure to the one disclosed in Example 10. Therefore, using the molecular weight of each component, the amounts of beta-cyclodextrin and NHDC contained in each amount of the combinations of Examples F and G were calculated and, then, the antibittering contribution of each component was calculated on the basis of the data of Table 19. The expected masking effect was calculated as the sum of the contributions of each component, and, finally, the masking synergy was calculated (using Formula IV).

The results for Examples F and G are disclosed in Tables 19 and 20, respectively.

TABLE 19

| [Ex. F] (ppm) | [bCD] (ppm) | Expected bCD masking contribution (%) | [NHDC] (ppm) | Expected NHDC masking contribution (%) | Expected masking effect (%) | Real masking effect (%) | Synergy (%) |
|---|---|---|---|---|---|---|---|
| 5 | 3.25 | 0.00 | 1.75 | 1.75 | 1.75 | 5.00 | 185.15 |
| 25 | 16.23 | 3.74 | 8.77 | 6.57 | 10.31 | 20.00 | 93.91 |
| 50 | 32.47 | 8.16 | 17.53 | 10.22 | 18.38 | 30.00 | 63.20 |
| 75 | 48.70 | 11.41 | 26.30 | 14.20 | 25.61 | 33.33 | 30.17 |
| 100 | 64.93 | 14.65 | 35.07 | 20.05 | 34.70 | 45.00 | 29.69 |

TABLE 20

| [Ex. G] (ppm) | [bCD] (ppm) | Expected bCD masking contribution (%) | [NHDC] (ppm) | Expected NHDC masking contribution (%) | Expected masking effect (%) | Real masking effect (%) | Synergy (%) |
|---|---|---|---|---|---|---|---|
| 5 | 4.24 | 0.00 | 0.76 | 0.76 | 0.76 | 1.67 | 118.49 |
| 25 | 21.19 | 5.40 | 3.81 | 3.81 | 9.21 | 15.00 | 62.88 |
| 50 | 42.37 | 10.14 | 7.63 | 6.10 | 16.24 | 31.67 | 95.04 |
| 75 | 63.56 | 14.38 | 11.44 | 7.68 | 22.06 | 40.00 | 81.30 |
| 100 | 84.74 | 15.37 | 15.26 | 9.27 | 24.64 | 48.33 | 96.15 |

Example 12: Masking Astringency of Green Tea Extract

Astringency taste masking capacity was measured using the same methodology as disclosed for bitter masking capability (Examples 10 and 11).

The following substances were assayed: a composition comprising NHDC and gamma-cyclodextrin in a molar ratio 1:3 (Example B) and a composition comprising NHDC and beta-cyclodextrin in a molar ratio 1:3 (Example G), as well as NHDC alone, gamma-cyclodextrin alone and beta-cyclodextrin alone. The evaluated taste maskers were dissolved in water, together with 5 ppm of green tea extract.

First, a calibrated taste panel compared a solution prepared with 30 ppm of Example G and 5 ppm of green tea extract to different base solutions of green tea extract in water, and determined the equally astringent base in water solution. Next, two solutions were prepared containing, respectively, the proportional amount of NHDC and beta-cyclodextrin contained in 30 ppm of Example G, together with 5 ppm of green tea extract, and the taste panel determined the equally astringent base in water solution for both solutions.

The masking effect for each substance was calculated using a formula analogous to Formula III (substituting 5000 with 5), and the astringency masking synergy between beta-cyclodextrin and NHDC in Example G was calculated using Formula IV.

The masking effects and astringency masking synergy between gamma-cyclodextrin and NHDC for 30 ppm of Example B were calculated analogously.

The results are shown in Table 21:

TABLE 21

| Ex. | [gCD] (ppm) | Expected gCD masking contribution (%) | [NHDC] (ppm) | Expected NHDC masking contribution (%) | Expected masking effect (%) | Real masking effect (%) | Synergy (%) |
| --- | --- | --- | --- | --- | --- | --- | --- |
| G | 25.60 | 28.00 | 4.40 | 10.00 | 38.00 | 50.00 | 33.33 |
| B | 25.92 | 19.00 | 4.08 | 8.00 | 27.00 | 33.00 | 23.26 |

Example 13: $^1$H NMR Characterization of the Complex NHDC:gCD

The composition of Example A is in the form of a complex having a 1:1 molar ratio NHDC:gCD. It was prepared as described in Examples 1 and 9.

Figure 5:
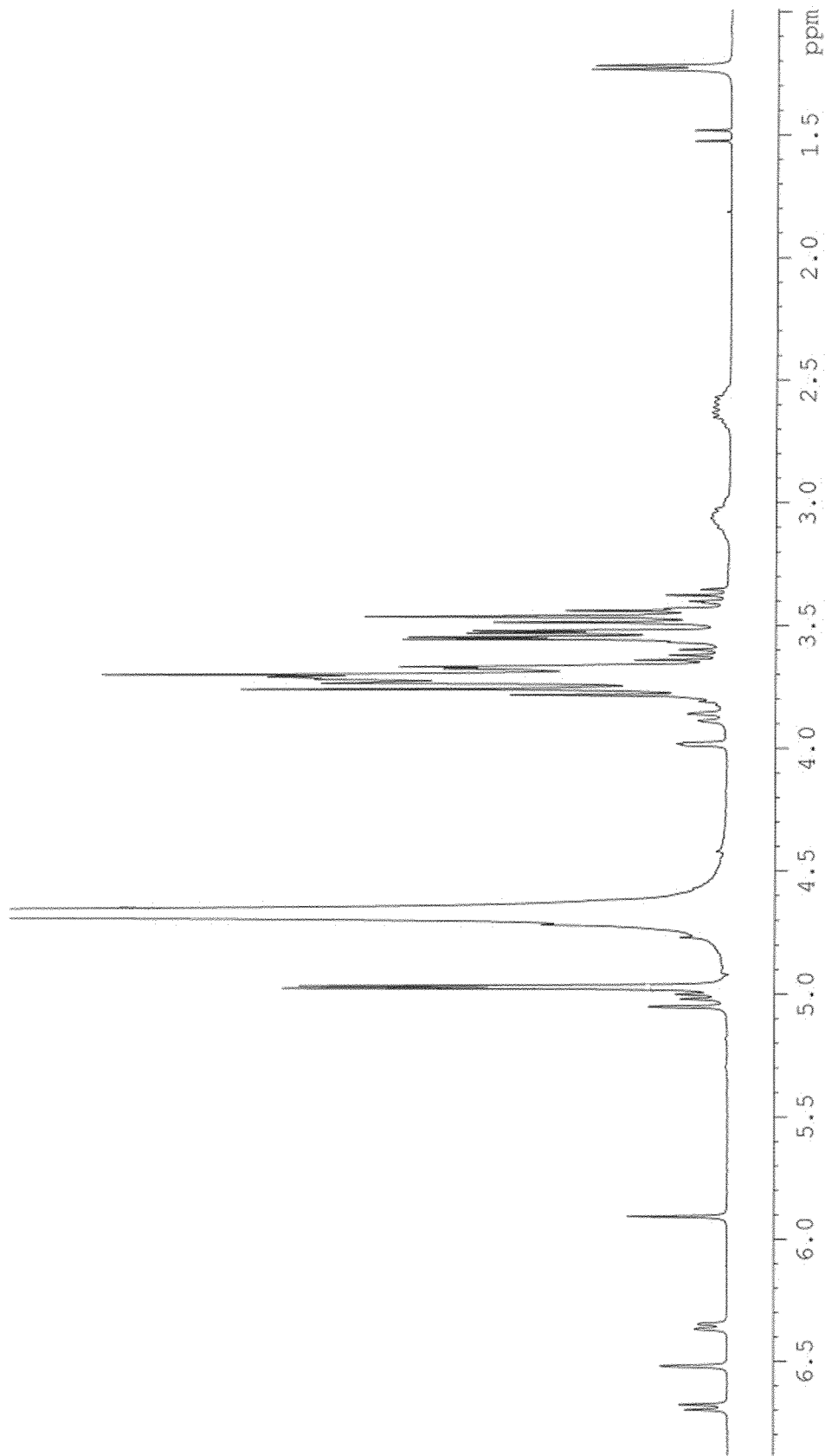
FIG. 5 represents the $^1$H-NMR spectrum in $D_2O$ at 400 MHz of the complex of Example A, having a 1:1 molar ratio NHDC:gamma-cyclodextrin.

The $^1$H NMR spectrum of this complex was recorded in $D_2O$ at 400 MHz, and is shown in FIG. 5.

Figure 6:
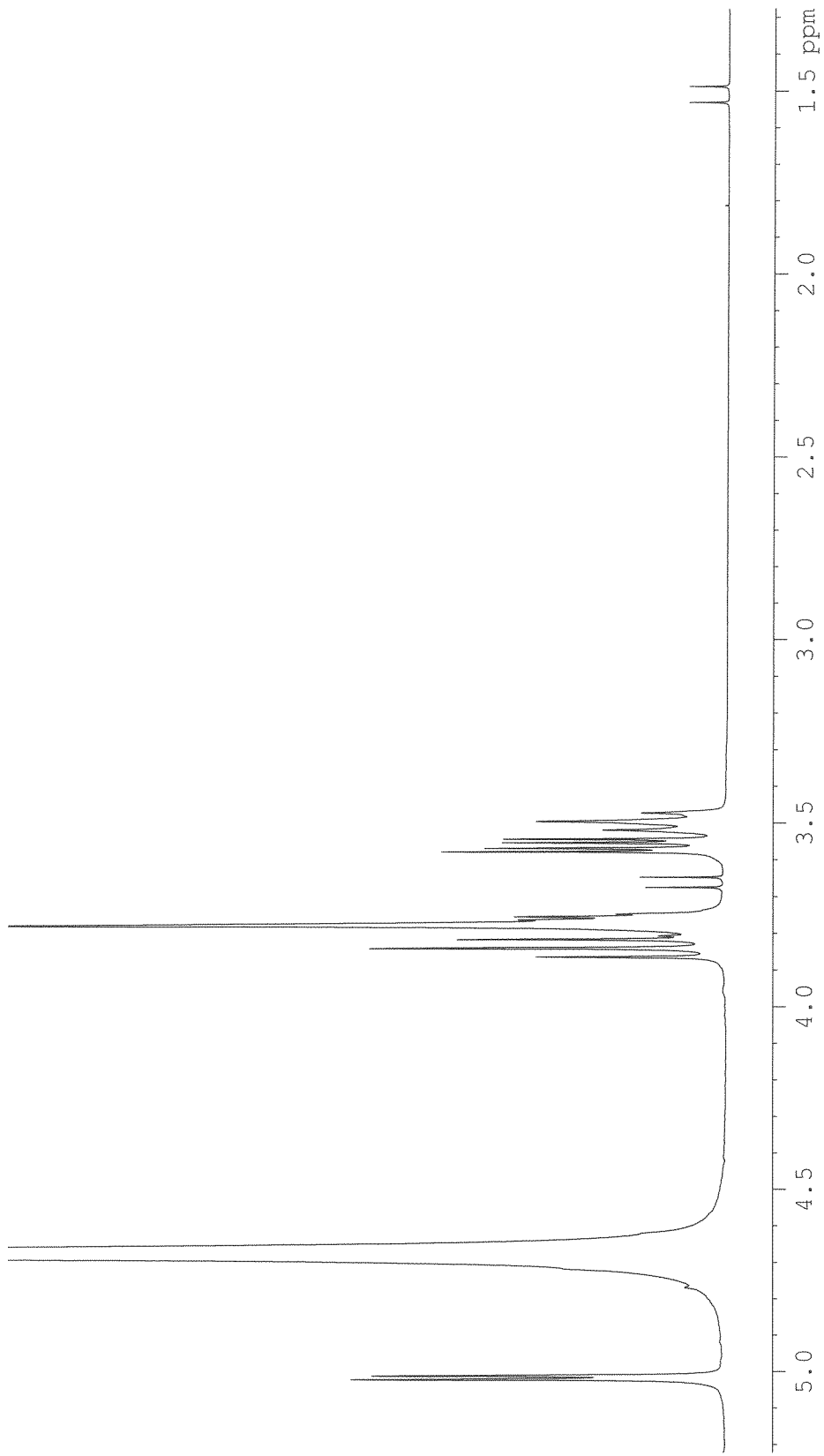
FIG. 6 represents the $^1$H-NMR spectrum in $D_2O$ at 400 MHz of gamma-cyclodextrin.
Figure 7:
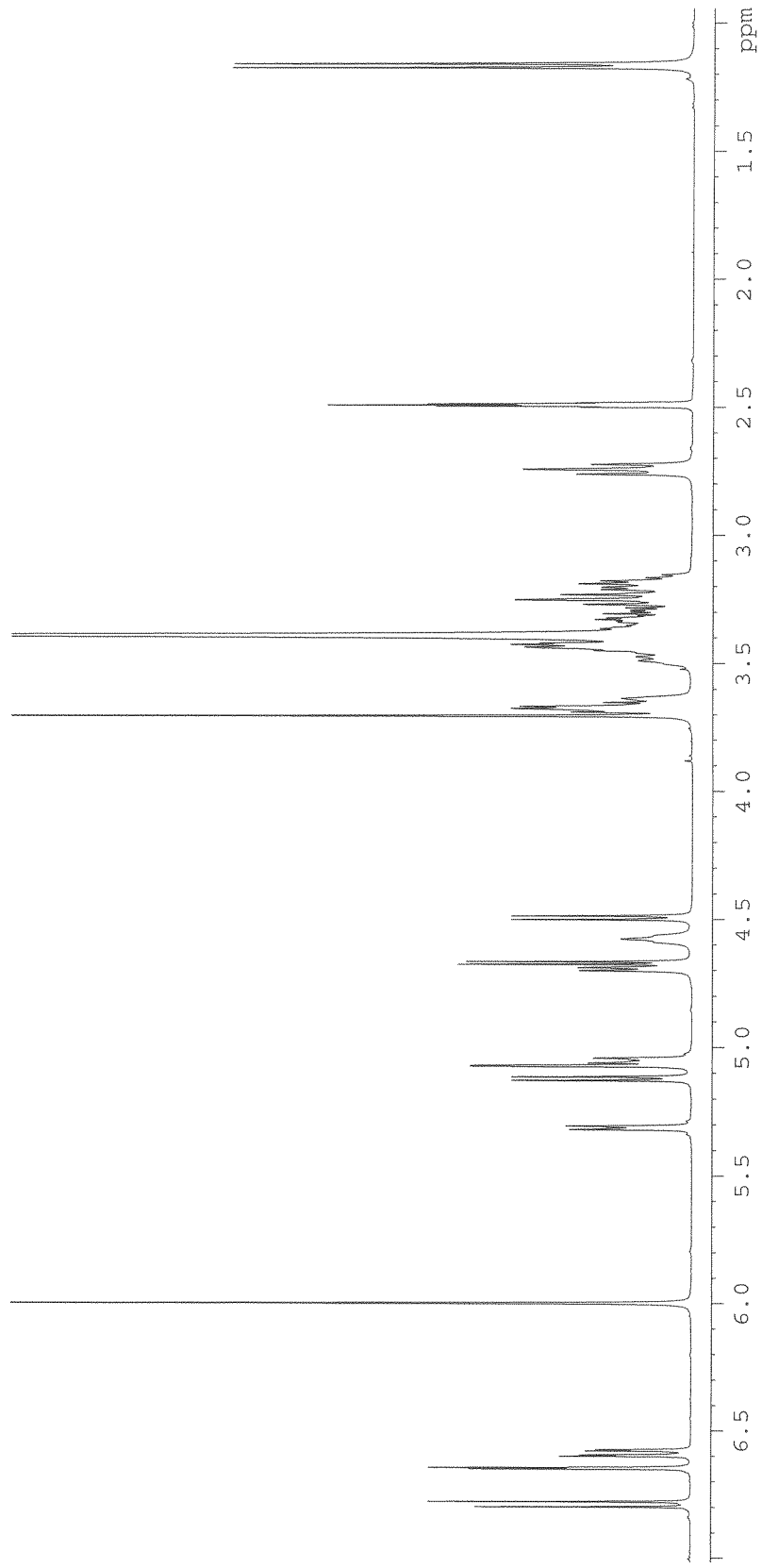
FIG. 7 represents the $^1$H-NMR spectrum in deuterated DMSO at 400 MHz of NHDC.

Furthermore, the $^1$H NMR of pure gamma-cyclodextrin in $D_2O$ at 400 MHz (FIG. 6) and the $^1$H NMR of pure NHDC in deuterated DMSO (DMSO-d6) at 400 MHz (FIG. 7) were also recorded and compared with the spectrum of the complex.

Figure 8:
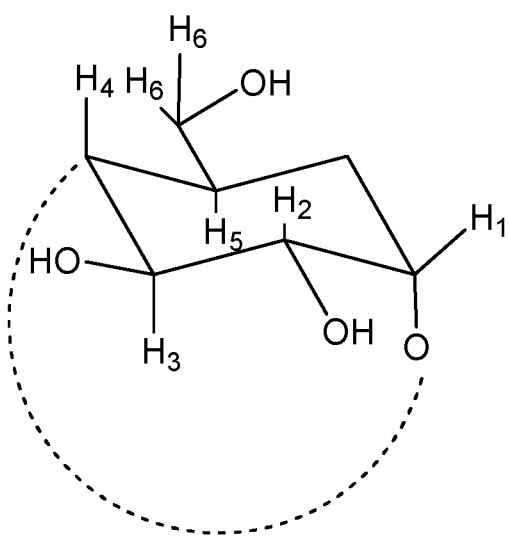
FIG. 8 schematically represents one glucopyranose ring forming part of the structure of gamma-cyclodextrin, wherein the protons as described in the $^1$H NMR spectrum are identified.

Table 22 below shows specifically the comparison in the chemical shifts in the $^1$H NMR for the protons H1 to H6 of pure gamma-cyclodextrin (FIG. 6) versus the chemical shifts of the equivalent protons in the complex (FIG. 5). Each proton in the gamma-CD is identified in the schematic formula shown in FIG. 8.

TABLE 22

| H in gamma-CD | gCD (δ (ppm)) | Example A (δ (ppm)) | Δδ (ppm) |
| --- | --- | --- | --- |
| $H_1$ | 5.016 | 4.971 | 0.045 |
| $H_2$ | 3.841 | 3.760 | 0.081 |
| $H_3$ | 3.561 | 3.540 | 0.021 |
| $H_4$ | 3.495 | 3.465 | 0.030 |
| $H_5$ | 3.759 | 3.673 | 0.086 |
| $H_6$ | 3.778 | 3.701 | 0.077 |

It can be observed that there is a variation in the chemical shifts in the complex compared to cyclodextrin alone (last column of the table).

Figure 9:
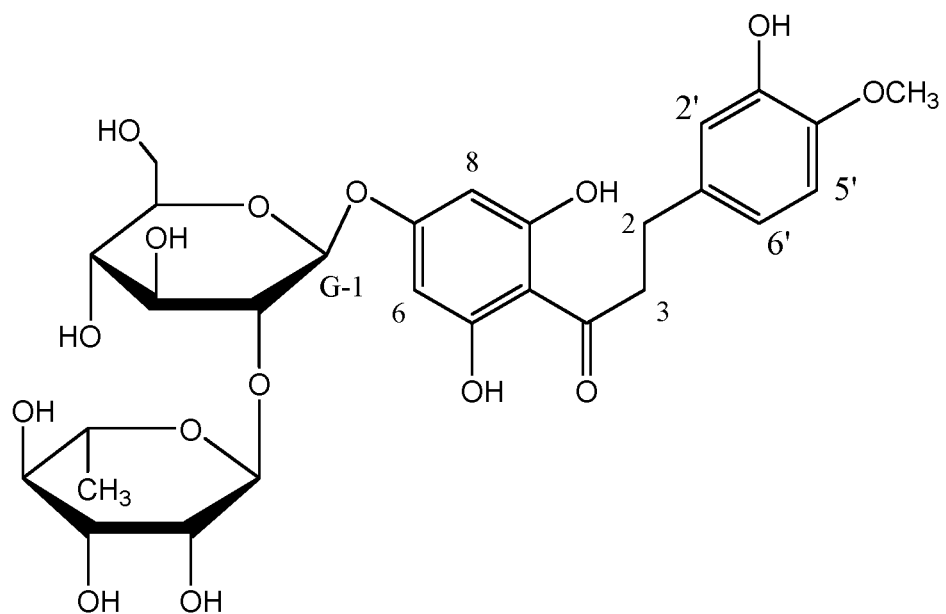
FIG. 9 schematically represents the aglycone part of the structure of neohesperidin dihydrochalcone, wherein the protons as described in the $^1$H NMR spectrum are identified.

Analogously, Table 23 below shows specifically the comparison in the chemical shifts in the $^1$H NMR for the protons of pure NHDC (FIG. 7) versus the chemical shifts of the equivalent protons when NHDC is forming part of the complex, in Example A (FIG. 5). Each proton in NHDC is identified in the schematic formula of FIG. 9.

TABLE 23

| H in NHDC | NHDC (δ (ppm)) | Example A (δ (ppm)) | Δδ (PPm) |
| --- | --- | --- | --- |
| H-5' | 6.788 | 6.688 | 0.100 |
| H-2' | 6.647 | 6.519 | 0.128 |
| H-6' | 6.587 | 6.357 | 0.230 |

TABLE 23-continued

| H in NHDC | NHDC (δ (ppm)) | Example A (δ (ppm)) | Δδ (PPm) |
| --- | --- | --- | --- |
| H-6 | 5.998 | 5.907 | 0.091 |
| H-8 | | 5.050 | 0.948 |
| G-1 | 5.121 | 5.010 | 0.111 |
| $CH_2$ (2) | 2.723(t) | 2.611(m) | 0.112 |
| $CH_2$ (3)** | 3.251(t) | 3.050(m) | 0.201 |

It can be observed that there is a variation in the chemical shifts in the complex compared to NHDC alone (last column of the table).

Furthermore, it can also be observed that protons H-6 and H-8, which are chemically equivalents in pure NHDC, are differentiated in the complex of Example A. Moreover, the protons in the methylene groups ($CH_2$) at positions 2 and 3, which appear as triplets in the $^1$H NMR of NHDC, appear as multiplets in the complex.

The invention claimed is:

1. Sweetening composition comprising neohesperidin dihydrochalcone and gamma-cyclodextrin, wherein the molar ratio of neohesperidin dihydrochalcone:gamma-cyclodextrin is comprised between 1.5:1 and 1:10.

2. Composition according to claim 1, wherein the molar ratio of neohesperidin dihydrochalcone:gamma-cyclodextrin is comprised between 1.5:1 and 1:6.

3. Composition according to claim 1, wherein the molar ratio of neohesperidin dihydrochalcone:gamma-cyclodextrin is about 1:1.

4. Composition according to claim 1, wherein the molar ratio of neohesperidin dihydrochalcone:gamma-cyclodextrin is 1±0.1: 1±0.1.

5. Composition according to claim 4, wherein the molar ratio of neohesperidin dihydrochalcone:gamma-cyclodextrin is 1±0.05: 1±0.05.

6. Composition according to claim 1, wherein the molar ratio of neohesperidin dihydrochalcone:gamma-cyclodextrin is about 1:3.

7. Composition according to claim 1, wherein the molar ratio of neohesperidin dihydrochalcone:gamma-cyclodextrin is 1±0.1: 3±0.3.

8. Composition according to claim 7, wherein the molar ratio of neohesperidin dihydrochalcone:gamma-cyclodextrin is 1±0.05: 3±0.15.

9. Process for sweetening an ingestible product comprising adding the sweetening composition of claim 1 to the ingestible product.

10. The process according to claim 9, wherein the ingestible product is selected from a food product and a pharmaceutical product.

11. Ingestible product comprising the sweetening composition according to claim 1.

* * * * *